(12) United States Patent
Liu et al.

(10) Patent No.: US 9,061,967 B2
(45) Date of Patent: Jun. 23, 2015

(54) SUBSTITUTED DIPHENYLAMINE COMPOUNDS, PREPARATION METHOD AND USE THEREOF

(75) Inventors: Changling Liu, Shenyang (CN); Huichao Li, Shenyang (CN); Zhinian Li, Shenyang (CN); Guang Huang, Shenyang (CN); Hong Zhang, Shenyang (CN)

(73) Assignees: Shenyang Research Institute Of Chemical Industry Co., LTD., Shenyang, Liaoning (CN); Sinochem Corporation, Beijing (CN)

( * ) Notice: Subject to any disclaimer, the term of this patent is extended or adjusted under 35 U.S.C. 154(b) by 359 days.

(21) Appl. No.: 13/578,787

(22) PCT Filed: Mar. 21, 2011

(86) PCT No.: PCT/CN2011/071983
§ 371 (c)(1),
(2), (4) Date: Aug. 13, 2012

(87) PCT Pub. No.: WO2011/116671
PCT Pub. Date: Sep. 29, 2011

(65) Prior Publication Data
US 2012/0309844 A1 Dec. 6, 2012

(30) Foreign Application Priority Data
Mar. 22, 2010 (CN) .......................... 2010 1 0129005

(51) Int. Cl.
| | |
|---|---|
| C07D 213/643 | (2006.01) |
| C07D 213/70 | (2006.01) |
| C07C 211/56 | (2006.01) |
| A01N 33/18 | (2006.01) |
| A01N 37/34 | (2006.01) |
| A01N 37/44 | (2006.01) |
| A01N 41/10 | (2006.01) |
| A01N 43/40 | (2006.01) |
| C07C 237/30 | (2006.01) |
| C07C 237/40 | (2006.01) |
| C07C 255/58 | (2006.01) |
| C07C 317/36 | (2006.01) |
| C07C 323/36 | (2006.01) |
| C07C 327/48 | (2006.01) |
| A01N 33/22 | (2006.01) |

(52) U.S. Cl.
CPC .............. *C07C 211/56* (2013.01); *A01N 33/18* (2013.01); *A01N 37/34* (2013.01); *A01N 37/44* (2013.01); *A01N 41/10* (2013.01); *A01N 43/40* (2013.01); *C07C 237/30* (2013.01); *C07C 237/40* (2013.01); *C07C 255/58* (2013.01); *C07C 317/36* (2013.01); *C07C 323/36* (2013.01); *C07C 327/48* (2013.01); *C07D 213/643* (2013.01); *C07D 213/70* (2013.01); *A01N 33/22* (2013.01)

(58) Field of Classification Search
CPC .......................... C07D 213/643; C07D 213/70
See application file for complete search history.

(56) References Cited

U.S. PATENT DOCUMENTS
| | | |
|---|---|---|
| 4,152,460 A | 5/1979 | Dreikorn |
| 4,304,791 A | 12/1981 | Clinton |

FOREIGN PATENT DOCUMENTS
| | | |
|---|---|---|
| CN | 1333205 A | 1/2002 |

OTHER PUBLICATIONS

International Search Report received in PCT/CN2011/071983, mailed Jun. 30, 2011. English translation provided.

*Primary Examiner* — Yong Chong
(74) *Attorney, Agent, or Firm* — Smith, Gambrell & Russell, LLP

(57) ABSTRACT

Substituted diphenylamine compounds of general formula I are provided, in which each substituted group is defined as in the description. The compounds of general formula I have broad-spectrum fungicidal activity in the field of agriculture. Furthermore, the preparation methods of the above compounds are simple.

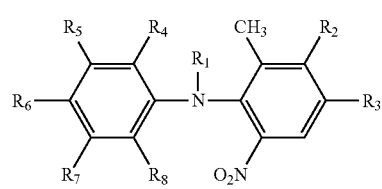

6 Claims, No Drawings

SUBSTITUTED DIPHENYLAMINE COMPOUNDS, PREPARATION METHOD AND USE THEREOF

FIELD OF THE INVENTION

The invention relates to fungicide in agricultural fields, specifically to a kind of substituted diphenylamine compounds and the preparation methods and use thereof.

BACKGROUND OF THE INVENTION

Diphenylamine and fluazinam are known fungicides, the former is mainly used to control storage diseases of fruits and vegetables, and the latter is mainly used to control diseases of field crops.

The compounds having the following general formulas were reported as insecticides, acaricides, fungicides, herbicides, rodenticides or others in the prior art:

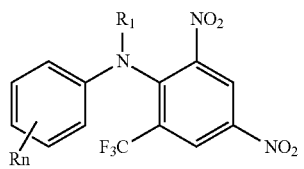

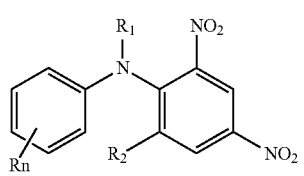

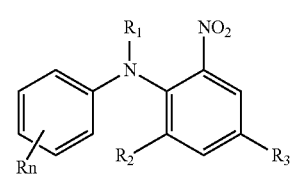

Such as patents BR7900462, CH626323, CN1188757, DE2509416, DE2642147, DE2642148, EP26743, EP60951, GB1544078, GB1525884, JP58113151, JP64001774, JP01186849, WO2002060878, WO2005035498, WO2009037707, U.S. Pat. No. 3,948,957, U.S. Pat. No. 3,948,990, U.S. Pat. No. 4,041,172, U.S. Pat. No. 4,152,460, U.S. Pat. No. 4,187,318, U.S. Pat. No. 4,215,145, U.S. Pat. No. 4,304,791, U.S. Pat. No. 4,316,988, U.S. Pat. No. 4,407,820, U.S. Pat. No. 4,459,304, U.S. Pat. No. 4,670,596 and so on, and ACS Symposium Series (1992), 504 (Synth. Chem. Agrochem. III), 336-48; Journal of the Chemical Society (1951), 110-15, etc. all reported the compounds having above general formulas.

In addition, the compounds of the following general formulas were mentioned in Chemische Berichte (1962), 95 1711-21; Chemische Berichte (1963), 96(7), 1936-44; Journal of Organic Chemistry (1954), 19, 1641-5; Journal of the Chemical Society; Transactions (1913), 103 982-8 and Journal of the Chemical Society, Transactions (1921), 119, 187-92 and so on, but without any bioactivity reported.

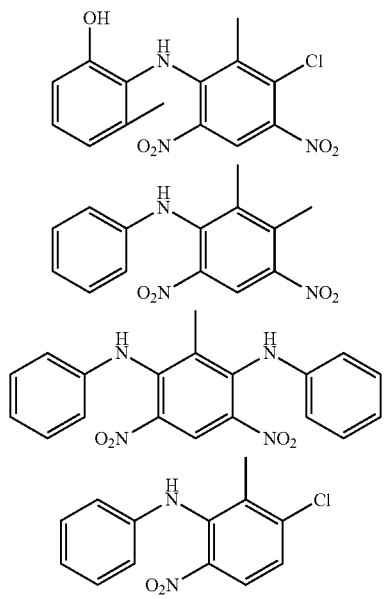

The preparation method of the following compound was published in U.S. Pat. No. 3,107,263:

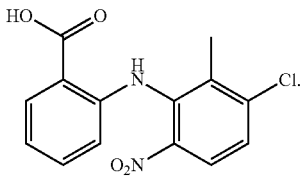

The compounds having the structure of general formula I were not reported in the prior art.

SUMMARY OF THE INVENTION

New pesticides with novel structure and excellent property are needed by modern agricultural production. The object of the present invention is to provide a kind of substituted diphenylamine compounds to control a variety of plant pathogens/diseases at very low doses, which can be used to prepare substances to control pathogens in agricultural and other fields.

Detailed descriptions of the invention are as follows:

The present invention provides a kind of substituted diphenylamine compounds having general formula I:

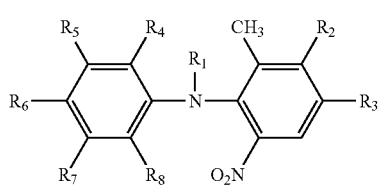

Wherein:

$R_1$ is selected from H, $C_1$-$C_{12}$alkyl, $C_3$-$C_{12}$cycloalkyl, $C_1$-$C_{12}$haloalkyl, $C_1$-$C_{12}$alkylcarbonyl, $C_1$-$C_{12}$haloalkylcarbonyl, $C_1$-$C_{12}$alkoxycarbonyl, $C_1$-$C_{12}$alkylaminocarbonyl, $C_1$-$C_{12}$alkylthio, $C_1$-$C_{12}$haloalkylthio, $C_1$-$C_{12}$alkylsulfonyl, $C_1$-$C_{12}$alkoxyl$C_1$-$C_{12}$alkyl, $C_1$-$C_{12}$alkoxy$C_1$-$C_{12}$alkylcarbonyl, $C_1$-$C_{12}$alkoxycarbonyl$C_1$-$C_{12}$alkyl, $C_1$-$C_{12}$alkylaminothio, $C_2$-$C_{12}$ dialkylaminothio or CO—X—$CO_2R_9$, in which X is selected from $(CHR_9)n$, $CR_9=CR_{10}$ or $C_6H_4$, n=1-6;

$R_2$ is selected from halogen, $C_1$-$C_{12}$haloalkyl, $C_1$-$C_{12}$alkoxy, $C_1$-$C_{12}$haloalkoxy, $C_1$-$C_{12}$alkylamino, $C_1$-$C_{12}$haloalkylamino, $C_1$-$C_{12}$alkylthio, $C_1$-$C_{12}$haloalkylthio, $C_1$-$C_{12}$alkylsulfonyl, $C_3$-$C_{12}$cycloalkyl, $C_2$-$C_{12}$dialkylamino, $C_3$-$C_{12}$alkenyloxy, $C_3$-$C_{12}$haloalkenyloxy, $C_3$-$C_{12}$alkynyloxy, $C_3$-$C_{12}$haloalkynyloxy, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxy$C_1$-$C_{12}$alkoxy, $C_1$-$C_{12}$alkoxycarbonyl$C_1$-$C_{12}$alkoxy, or the following groups unsubstituted or substituted with 1-5 $R_{11}$: aryloxy, arylamino, arylmethoxy, arylmethyl amino, heteroaryloxy or heteroarylamino, and when the number of the substitutes is more than 1, $R_{11}$ may be the same or different;

$R_3$ is selected from H, halogen, $NO_2$, CN, $C(=O)NR_9R_{10}$, $C(=S)NR_9R_{10}$, $C_1$-$C_{12}$alkylaminocarbonyl, $C_1$-$C_{12}$alkoxycarbonyl, $C_1$-$C_{12}$haloalkyl or $C_1$-$C_{12}$alkylsulfonyl;

$R_4$ and $R_8$ may be the same or different, respectively selected from H, halogen, CN, $NO_2$, OH, $CO_2H$, $C(=O)NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkylcarbonyloxy, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

$R_5$ and $R_7$ may be the same or different, respectively selected from H, halogen, CN, $NO_2$, OH, $CO_2H$, $C(=O)NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylamino, $C_1$-$C_{12}$haloalkylamino, $C_1$-$C_{12}$alkylthio, $C_1$-$C_{12}$haloalkylthio, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkylcarbonyloxy, $C_1$-$C_{12}$alkoxycarbonyloxy, $C_1$-$C_{12}$alkylaminocarbonyloxy, $C_1$-$C_{12}$alkylsulfonyloxy, $C_1$-$C_{12}$alkoxy$C_1$-$C_{12}$alkoxy, $C_1$-$C_{12}$haloalkoxy$C_1$-$C_{12}$haloalkoxy, $C_1$-$C_{12}$alkoxycarbonyl$C_1$-$C_{12}$alkoxy, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

$R_6$ is selected from H, halogen, CN, $NO_2$, OH, $CO_2H$, $C(=O)NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkoxy$C_1$-$C_{12}$alkoxy, $C_1$-$C_{12}$haloalkoxy$C_1$-$C_{12}$haloalkoxy, $C_1$-$C_{12}$alkylcarbonyloxy, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

But $R_4$, $R_5$, $R_6$, $R_7$ and $R_8$ can not be H simultaneously;

$R_9$ and $R_{10}$ may be the same or different, respectively selected from H or $C_1$-$C_6$alkyl;

$R_{11}$ is selected from halogen, $NO_2$, CN, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylcarbonyl, $C_1$-$C_6$alkoxycarbonyl, $C_2$-$C_6$alkenyl, $C_2$-$C_6$haloalkenyl, $C_3$-$C_6$alkenyloxy, $C_3$-$C_6$haloalkenyloxy, $C_2$-$C_6$alkynyl, $C_2$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$haloalkylamino, $C_2$-$C_8$dialkylamino, $C_1$-$C_6$alkylcarbonylamino, $C_1$-$C_6$haloalkylcarbonylamino, $C_1$-$C_6$alkylaminocarbonyl or $C_1$-$C_6$haloalkylaminocarbonyl;

Or the salts of the compounds having general formula I.

The preferred compounds of general formula I of this invention are:

$R_1$ is selected from H, $C_1$-$C_6$alkyl, $C_3$-$C_6$cycloalkyl, $C_1$-$C_6$alkylcarbonyl, $C_1$-$C_6$haloalkylcarbonyl, $C_1$-$C_6$alkoxycarbonyl, $C_1$-$C_6$alkylthio, $C_1$-$C_6$haloalkylthio, $C_1$-$C_6$alkylsulfonyl, $C_1$-$C_6$alkoxy$C_1$-$C_6$alkyl, $C_1$-$C_6$alkoxy$C_1$-$C_6$alkylcarbonyl, $C_1$-$C_6$alkoxycarbonyl$C_1$-$C_6$alkyl, $C_1$-$C_6$alkylaminothio, $C_2$-$C_6$ dialkylaminothio or CO—X—$CO_2R_9$, in which X is selected from $(CHR_9)n$, $CR_9=CR_{10}$ or $C_6H_4$, n=1-3;

$R_2$ is selected from halogen, $C_1$-$C_6$alkoxy, $C_1$-$C_6$haloalkoxy, $C_1$-$C_6$alkylamino, $C_1$-$C_6$haloalkylamino, $C_1$-$C_6$alkylthio, $C_1$-$C_6$haloalkylthio, $C_1$-$C_6$alkylsulfonyl, $C_2$-$C_6$dialkylamino, $C_3$-$C_6$alkenyloxy, $C_3$-$C_6$haloalkenyloxy, $C_3$-$C_6$alkynyloxy, $C_1$-$C_6$alkylcarbonyloxy, $C_1$-$C_6$alkylcarbonylamino, $C_1$-$C_6$alkylsulfonyloxy, $C_1$-$C_6$alkoxy$C_1$-$C_6$alkoxy, $C_1$-$C_6$alkoxycarbonyl$C_1$-$C_6$alkoxy, or the following groups unsubstituted or substituted with 1-3 $R_{11}$: phenoxy, anilino, benzyloxy, benzylamino, pyridyloxy or pyridylamino;

$R_3$ is selected from Cl, Br, F, $NO_2$, CN, $C(=O)NR_9R_{10}$, $C(=S)NR_9R_{10}$, $CO_2CH_3$, $CF_3$ or $SO_2CH_3$;

$R_4$ and $R_8$ may be the same or different, respectively selected from H, halogen, CN, $NO_2$, $C(=O)NR_9R_{10}$, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, or the following groups unsubstituted or substituted with 1-4 $R_{11}$: phenoxy, anilino, phenylcarbonyl, benzylcarbonyl, phenoxycarbonyl, anilinocarbonyl or pyridyloxy;

$R_5$ and $R_7$ may be the same or different, respectively selected from H, halogen, CN, $NO_2$, $C(=O)NR_9R_{10}$, $C_1$-$C_6$alkyl, $C_1$-$C_6$haloalkyl, $C_1$-$C_6$alkoxy, $C_1$-$C_6$haloalkoxy, $C_1$-$C_6$alkylamino, $C_1$-$C_6$haloalkylamino, $C_1$-$C_6$alkylthio, $C_1$-$C_6$haloalkylthio, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl or $C_1$-$C_6$alkoxy$C_1$-$C_6$alkyl;

$R_6$ is selected from H, halogen, CN, $NO_2$, $CO_2H$, $C(=O)NR_9R_{10}$, $C_1$-$C_6$alkyl, $C_1$-$C_6$haloalkyl, $C_1$-$C_6$haloalkoxy, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, $C_1$-$C_6$alkoxy$C_1$-$C_6$alkoxy, or the following groups unsubstituted or substituted with 1-4 $R_{11}$: phenoxy, anilino, phenylcarbonyl, benzylcarbonyl, phenoxycarbonyl, anilinocarbonyl or pyridyloxy;

But $R_4$, $R_5$, $R_6$, $R_7$ and $R_8$ can not be H simultaneously;

$R_9$ and $R_{10}$ may be the same or different, respectively selected from H or $C_1$-$C_3$alkyl;

$R_{11}$ is selected from halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylcarbonyl, $C_1$-$C_3$alkoxycarbonyl, $C_1$-$C_3$alkylamino, $C_2$-$C_6$dialkylamino, $C_1$-$C_3$alkylcarbonylamino or $C_1$-$C_3$alkylam inocarbonyl;

Or the salts of the compounds having general formula I.

Furthermore, the preferred compounds of general formula I of this invention are:

$R_1$ is selected from H, $C_1$-$C_3$alkyl, $C_3$-$C_6$cycloalkyl, $C_1$-$C_3$alkylcarbonyl, $C_1$-$C_3$haloalkylcarbonyl, $C_1$-$C_3$alkoxycarbonyl, $C_1$-$C_3$haloalkylthio, $C_1$-$C_3$alkylsulfonyl, $C_1$-$C_3$alkoxy$C_1$-$C_3$alkyl, $C_1$-$C_3$alkoxy$C_1$-$C_3$alkylcarbonyl, $C_1$-$C_3$alkoxycarbonyl$C_1$-$C_3$alkyl, $C_1$-$C_3$alkylaminothio, $C_2$-$C_6$dialkylaminothio or CO—X—$CO_2R_9$, in which X is selected from $(CHR_9)n$, $CR_9=CR_{10}$ or $C_6H_4$, n=1-3;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_2$-$C_6$dialkylamino, $C_3$-$C_4$alkenyloxy, $C_3$-$C_4$haloalkenyloxy, $C_3$-$C_4$alkynyloxy, $C_1$-$C_3$alkylcarbonyloxy, $C_1$-$C_3$alkylcarbonylamino, $C_1$-$C_3$alkylsulfonyloxy, $C_1$-$C_3$alkoxy$C_1$-$C_3$alkoxy, $C_1$-$C_3$alkoxycarbonyl$C_1$-$C_3$alkoxy, or the following groups unsubstituted or substituted with 1-3 $R_{11}$: phenoxy, anilino, benzyloxy, benzylamino, pyridyloxy or pyridylamino;

$R_3$ is $NO_2$;

$R_4$ and $R_8$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_3$alkyl, $C_1$-$C_3$alkoxycarbonyl$C_1$-$C_3$alkyl, or the following groups unsubstituted or substituted with 1-3 $R_{11}$: phenoxy, anilino, phenylcarbonyl, benzylcarbonyl, phenoxycarbonyl, anilinocarbonyl or pyridyloxy;

$R_5$ and $R_7$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl or $C_1$-$C_3$alkoxy$C_1$-$C_3$alkyl;

$R_6$ is selected from H, Cl, Br, F, CN, $NO_2$, $CO_2H$, $C(=O)NR_9R_{10}$, $C_1$-$C_3$alkyl, $C_1$-$C_3$haloalkyl, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_6$alkyl, $C_1$-$C_3$alkoxycarbonyl$C_1$-$C_3$alkyl, $C_1$-$C_3$alkoxy$C_1$-$C_3$alkoxy, or the following groups unsubstituted or substituted with 1-3 $R_{11}$: phenoxy, anilino, phenylcarbonyl, benzylcarbonyl, phenoxycarbonyl, anilinocarbonyl or pyridyloxy;

But $R_4$, $R_5$, $R_6$, $R_7$ and $R_8$ can not be H simultaneously;

$R_9$ and $R_{10}$ may be the same or different, respectively selected from H or $C_1$-$C_3$alkyl;

$R_{11}$ is selected from Cl, Br, F, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylcarbonyl, $C_1$-$C_3$alkoxycarbonyl or $C_1$-$C_3$alkylaminocarbonyl;

Or the salts formed from the compounds of general formula I with hydrochloric acid, sulfuric acid, phosphoric acid, formic acid, acetic acid, trifluoroacetic acid, methylsulfonic acid, p-toluenesulfonic acid, malic acid or citric acid.

Even more preferred compounds of general formula I of this invention are:

$R_1$ is selected from H, $C_1$-$C_3$alkyl, $C_3$-$C_6$cycloalkyl, $C_1$-$C_3$alkylcarbonyl, $C_1$-$C_3$haloalkylcarbonyl, $C_1$-$C_3$alkoxycarbonyl, $C_1$-$C_3$haloalkylthio, $C_1$-$C_3$alkylsulfonyl, $C_1$-$C_3$alkoxy$C_1$-$C_3$alkyl, $C_1$-$C_3$alkoxy$C_1$-$C_3$alkylcarbonyl, $C_1$-$C_3$alkoxycarbonyl$C_1$-$C_3$alkyl, $C_1$-$C_3$alkylaminothio, $C_2$-$C_6$dialkylaminothio, $COCH_2CO_2R_9$, $COCH_2CH_2CO_2R_9$, $COCHCH_3CO_2R_9$, $COC_6H_4CO_2R_9$ or $COCH=CHCO_2R_9$;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_2$-$C_6$dialkylamino, $C_3$-$C_4$alkenyloxy, $C_3$-$C_4$haloalkenyloxy, $C_3$-$C_4$alkynyloxy, $C_1$-$C_3$alkoxy$C_1$-$C_3$alkoxy, $C_1$-$C_3$alkoxycarbonyl$C_1$-$C_3$alkoxy, or the following groups unsubstituted or substituted with 1-3 $R_{11}$: phenoxy, anilino, benzyloxy, benzylamino, pyridyloxy or pyridylamino;

$R_3$ is $NO_2$;

$R_4$ and $R_8$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_3$alkyl, $C_1$-$C_3$alkoxycarbonyl$C_1$-$C_3$alkyl, or the following groups unsubstituted or substituted with 1-3 $R_{11}$: phenoxy, anilino, phenoxycarbonyl or anilinocarbonyl;

$R_5$ and $R_7$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_1$-$C_3$alkylcarbonyl, $C_1$-$C_3$alkoxycarbonyl or $C_1$-$C_3$alkoxy$C_1$-$C_3$alkyl;

$R_6$ is selected from H, Cl, Br, F, CN, $NO_2$, $CO_2H$, $C(=O)NR_9R_{10}$, $C_1$-$C_3$alkyl, $C_1$-$C_3$haloalkyl, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_6$alkyl, $C_1$-$C_3$alkoxycarbonyl$C_1$-$C_3$alkyl, $C_1$-$C_3$alkoxy$C_1$-$C_3$alkoxy, or the following groups unsubstituted or substituted with 1-3 $R_{11}$: phenoxy, phenylcarbonyl, benzylcarbonyl, phenoxycarbonyl or anilinocarbonyl;

But $R_4$, $R_5$, $R_6$, $R_7$ and $R_8$ can not be H simultaneously;

$R_9$ and $R_{10}$ may be the same or different, respectively selected from H, $CH_3$ or $C_2H_5$;

$R_{11}$ is selected from Cl, Br, F, $NO_2$, CN, $CF_3$, $CH_3$, $OCH_3$, $SCH_3$, formyl, $CO_2CH_3$ or $CONHCH_3$;

Or the salts formed from the compounds of general formula I with hydrochloric acid, sulfuric acid, phosphoric acid, formic acid, acetic acid, trifluoroacetic acid, methylsulfonic acid, p-toluenesulfonic acid, malic acid or citric acid.

The most preferred compounds of formula I of this invention are:

$R_1$ is selected from H, $CH_3$, $C_2H_5$, cyclopropyl, formyl, $COCH_3$, $COCF_3$, $CO_2CH_3$, $CO_2C_2H_5$, $SCCl_3$, $SO_2CH_3$, $SO_2C_2H_5$, $CH_2OCH_3$, $CH_2OC_2H_5$, $CH_2CH_2OCH_3$, $COCH_2OCH_3$, $CH_2COOCH_3$, $SNHCH_3$, $SN(CH_3)_2$, $COCH_2CO_2H$, $COCH_2CO_2CH_3$, $COCH_2CH_2CO_2H$, $COCH_2CH_2CO_2CH_3$, $COCHCH_3CO_2H$, $COCHCH_3CO_2CH_3$, $COC_6H_4CO_2H$, $COC_6H_4CO_2CH_3$, $COCH=CHCO_2H$ or $COCH=CHCO_2CH_3$;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $SCH_3$, $SC_2H_5$, $N(CH_3)_2$, $N(C_2H_5)_2$, $OCH_2OCH_3$, OPh, NHPh, $OCH_2Ph$, $NHCH_2Ph$, 4-chlorophenoxy, 4-chlorophenylamino, 2-chloro-4-(trifluoromethyl)phenoxy, 2-chloro-4-

(trifluorom ethyl)phenylamino, 3-chloro-5-(trifluoromethyl) pyridin-2-yloxy or 3-chloro-5-(trifluoromethyl)pyridin-2-ylamino;

$R_3$ is $NO_2$;

$R_4$ and $R_8$ may be the same or different, respectively selected from H, Cl, Br, F, CN, $NO_2$, C(=O)$NH_2$, C(=O)$NHCH_3$, C(=O)N($CH_3$)$_2$, $CH_3$, $C_2H_5$, $CF_3$, $OCH_3$, $OC_2H_5$, $OCF_3$, $SO_2CH_3$, $SO_2C_2H_5$, $COCH_3$, $COC_2H_5$, $CO_2CH_3$, $CO_2C_2H_5$, OPh, NHPh, $CO_2Ph$ or CONHPh;

$R_5$ and $R_7$ may be the same or different, respectively selected from H, Cl, Br, F, CN, $NO_2$, C(=O)$NH_2$, $CH_3$, $CF_3$, $OCH_3$, $OCF_3$, $NHCH_3$, $SCH_3$, $SO_2CH_3$, $SO_2C_2H_5$, $COCH_3$, $COC_2H_5$, $CO_2CH_3$, $CO_2C_2H_5$ or $CH_2OCH_3$;

$R_6$ is selected from H, Cl, Br, F, CN, $NO_2$, $CO_2H$, C(=O)$NH_2$, C(=O)$NHCH_3$, C(=O)N($CH_3$)$_2$, $CH_3$, $CF_3$, CF($CF_3$)$_2$, $OCF_3$, $OCH_2CF_3$, $OCF_2CHFCF_3$, $SO_2CH_3$, $SO_2C_2H_5$, $COCH_3$, $COC_2H_5$, $CO_2CH_3$, $CO_2C_2H_5$, OPh, NHPh, COPh, $COCH_2Ph$, $CO_2Ph$, CONHPh, pyridinoxy or 3-chloro-5-(trifluoromethyl)pyridin-2-yloxy;

But $R_4$, $R_5$, $R_6$, $R_7$ and $R_8$ can not be H simultaneously;

Or the salts formed from the compounds of general formula I with hydrochloric acid, sulfuric acid, phosphoric acid, trifluoroacetic acid, methylsulfonic acid or p-toluenesulfonic acid.

The terms used above to definite the compounds of general formula I represent substitutes as follow:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkoxy" refers to straight or branched chain alkyl, which is linked to the structure by oxygen atom.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "alkylthio" refers to straight or branched chain alkyl, which is linked to the structure by sulfur atom.

The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "alkylamino" refers to straight or branched chain alkyl, which is linked to the structure by nitrogen atom.

The "haloalkylamino" refers to straight or branched chain alkylamino, in which hydrogen atoms may be all or partly substituted with halogen.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl.

The "haloalkenyl" stands for straight or branched chain alkenyl, in which hydrogen atoms can be all or partly substituted with halogen.

The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl.

The "haloalkynyl" stands for straight or branched chain alkynyl, in which hydrogen atoms can be all or partly substituted with halogen.

The "aryl" and "aryl" in arylalkyl, aryloxy and aryloxyalkyl include phenyl or naphthyl, etc.

The "heteroaryl" stands for five member ring or six member ring containing one or more N, O, S hetero atoms. Such as furanyl, pyrazolyl, thiazolyl, pyridinyl, pyrimidinyl, pyrazinyl, pyridazinyl, triazinyl, quinolinyl, etc.

Part of the substitutes of $R_1$, $R_2$, $R_4$, $R_5$, $R_6$, $R_7$ and $R_8$ in formula I are separately listed in table 1, table 2, table 3, table 4 and table 5, but without being restricted thereby.

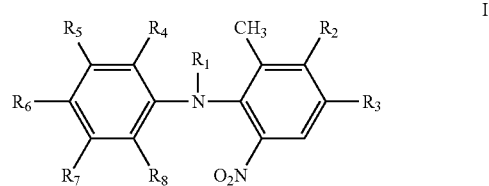

I

TABLE 1

| substitute $R_1$ |
|---|
| $R_1$ |
| H |
| $CH_3$ |
| $CH_2CH_3$ |
| $CH_2CH_2CH_3$ |
| $CH_2CH_2CH_2CH_3$ |
| $COCH_3$ |
| $COCH_2CH_3$ |
| $COCH_2CH_2CH_3$ |
| $CO_2CH_3$ |
| $CO_2CH_2CH_3$ |
| $COCH_2CO_2CH_3$ |
| $CH_2CH=CH_2$ |
| $CH_2CH_2CH=CF_2$ |
| $CH_2C\equiv CH$ |
| $COCH=CH_2CO_2H$ |
| $COCH=CH_2CO_2CH_3$ |
| $CO_2CH_3$ |
| ![cyclopropylmethyl] |
| $CO_2CH_2CH_2CH_3$ |
| $CONHCH_3$ |
| $CONHCH_2CH_3$ |
| $SO_2CH_3$ |
| $SO_2CH_2CH_3$ |
| $SCCl_3$ |
| $CH_2OCH_3$ |
| $CH_2CH_2OCH_3$ |
| $CH_2CH_2OCH_2CH_3$ |
| $CH_2CO_2CH_3$ |
| $COCH_2CH_2CO_2CH_3$ |
| $CH_2CH=CCl_2$ |
| $CH_2CH_2CF=CF_2$ |
| $CH_2C\equiv C-I$ |

TABLE 1-continued substitute $R_1$

$R_1$

[structure: 2-(methoxycarbonyl)phenyl ketone with methyl branch]

CH₂CO₂CH₂CH₃ — written as $CH_2CO_2CH_2CH_3$

- $CH_2CO_2CH_2CH_3$
- $COCH_2OCH_3$
- $COCH_2OCH_2CH_3$
- $SNHCH_3$
- $SNHCH_2CH_3$
- $SN(CH_3)_2$
- $SN(CH_2CH_3)_2$
- $COCH_2CO_2H$
- $COCH_2CH_2CO_2H$
- $COCHCH_3CO_2H$
- $COCHCH_3CO_2CH_3$
- $CH_2CH{=}CF_2$
- $CH_2CHF_2$
- $CH_2C{\equiv}CCH_3$

[structure: 2-carboxyphenyl ketone with methyl branch]

TABLE 2 substitute $R_2$

$R_2$

- F
- Cl
- Br
- I
- $CF_3$
- $OCH_3$
- $OCH_2CH_3$
- $OCH(CH_3)_2$

[structure: 3-chloro-2-oxy-5-(trifluoromethyl)pyridine]

- $OCF_3$
- $OCH_2CF_3$
- $NHCH_3$
- $N(CH_3)_2$
- $NHCH_2CH_3$
- $NH(CH_2)_2CH_3$
- $NHCH(CH_3)_2$
- $NHCH_2CF_3$

[structure: 2-chloro-3-chloro-5-(trifluoromethyl)pyridine variant]

- $SCH_3$
- $SCH_2CH_3$
- $SO_2CH_3$

TABLE 2-continued substitute $R_2$

$R_2$

- $SO_2CH_2CH_3$
- $OCH_2CH{=}CH_2$
- $OCH_2CH{=}CCl_2$
- $OCH_2C{\equiv}CH$
- $OCOCH_3$
- $OCH_2Ph$
- $NHCH_2Ph$
- $OCOCH_2CH_3$
- $NHCOCH_3$
- $NHCOCH_2CH_3$
- OPh
- OPh-4-Cl
- OPh-2-Cl—4$CF_3$
- OPh-2-Cl—4$NO_2$
- NHPh
- NHPh-4-Cl
- NHPh-2-Cl—4$CF_3$

TABLE 3 substitute $R_4(R_8)$

$R_4(R_8)$

- H
- F
- Cl
- Br
- I
- CN
- $NO_2$
- $CONH2$
- $CONHCH_3$
- $CON(CH_3)_2$
- $CONHCH_2CH_3$
- $CON(CH_2CH_3)_2$
- $CONH(CH_2)_2CH_3$
- $CONHCH(CH_3)_2$
- $OCF_3$
- OH
- $CH_3$
- $CH_2CH_3$
- $(CH_2)_2CH_3$
- $CH(CH_3)_2$
- $CF_3$
- $CHF_2$
- $CH_2F$
- $CH_2CF_3$
- $CF_2CHF_2$
- $CF_2CF_3$
- $OCH_3$
- $OCH_2CH_3$
- $O(CH_2)_2CH_3$
- $OCH(CH_3)_2$
- $OCH_2CF_3$
- $OCOCH_3$
- $CH{=}CH_2$
- $CH_2CH{=}CH_2$
- $C{\equiv}CH$
- $CH_2C{\equiv}CH$
- $SO_2CH_3$
- $SO_2CH_2CH_3$
- $COCH_3$
- $COCH_2CH_3$
- $CO_2CH_3$
- $CO_2CH_2CH_3$
- $CH_2OCH_3$
- $CH_2OCH_2CH_3$
- $CH_2CO_2CH_3$
- $CH_2CO_2CH_2CH_3$
- $OCF_2CF_3$
- $CO_2H$
- Ph TABLE 3-continued substitute R4(R8)

R4(R8)

CH2Ph
OPh
NHPh
COPh
CO2Ph
CO2Ph-4-Cl
CO2Ph-2-Cl-4-CF3
CO2Ph-2-Cl-4-NO2
CONHPh
CONHPh-4-Cl
CONHPh-2-Cl-4-CF3
CONHPh-2-Cl-4-NO2

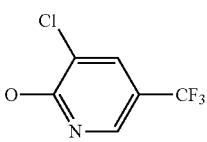 [SMILES: Oc1ncc(C(F)(F)F)cc1Cl]

TABLE 4 substitute R5(R7)

R5(R7)

H
F
Cl
Br
I
CN
NO2
CONH2
CONHCH3
CON(CH3)2
CONHCH2CH3
CON(CH2CH3)2
CONH(CH2)2CH3
CONHCH(CH3)2
OSO2CH2CH3
OCH2OCH3
OCH2OCH2CH3
OCH2CO2CH3
COPh
OH
CH3
CH2CH3
(CH2)2CH3
CH(CH3)2
CF3
CHF2
CH2F
CH2CF3
CF2CHF2
CF2CF3
OCH3
OCH2CH3
O(CH2)2CH3
OCH(CH3)2
Ph
CH2Ph
OPh
NHPh
CONHPh
CO2H
OCF3
OCH2CF3
OCF2CF3
NHCH3
NHCH2CH3
NHCH2CF3
SCH3

TABLE 4-continued substitute R5(R7)

R5(R7)

SCH2CH3
CH=CH2
CH2CH=CH2
C≡CH
CH2C≡CH
SO2CH3
SO2CH2CH3
CO2Ph
CO2Ph-4-Cl
CO2Ph-2-Cl-4-CF3
CO2Ph-2-Cl-4-NO2
COCH2Ph
COCH2Ph-4-Cl
COCH3
COCH2CH3
CO2CH3
CO2CH2CH3
CH2OCH3
CH2OCH2CH3
CH2CO2CH3
CH2CO2CH2CH3
OCOCH3
OCOCH2CH3
OCO2CH3
OCO2CH2CH3
OCONHCH3
OCONHCH2CH3
OSO2CH3
CONHPh-4-Cl
CONHPh-2-Cl-4-CF3

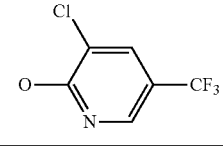

TABLE 5 substitute R6

R6

H
F
Cl
Br
I
CN
NO2
CONH2
CONHCH3
CON(CH3)2
CONHCH2CH3
CON(CH2CH3)2
CONH(CH2)2CH3
CO2Ph
CONHPh
OH
CONHCH(CH3)2
CH3
CH2CH3
(CH2)2CH3
CH(CH3)2
CF3
CHF2
CH2F
CH2CF3
CF2CHF2
CF2CF3
OCH3
OCH2CH3

TABLE 5-continued substitute $R_6$ $R_6$

CO$_2$Ph-4-Cl
CONHPh-4-Cl
OCOCH$_3$
O(CH$_2$)$_2$CH$_3$
OCH(CH$_3$)$_2$
OCF$_3$
OCH$_2$CF$_3$
CH=CH$_2$
CH$_2$CH=CH$_2$
C≡CH
CH$_2$C≡CH
SO$_2$CH$_3$
SO$_2$CH$_2$CH$_3$
COCH$_3$
COCH$_2$CH$_3$
CO$_2$CH$_3$
CO$_2$Ph-2-Cl-4-CF$_3$
CONHPh-2-Cl-4-CF$_3$
CO$_2$H
CO$_2$CH$_2$CH$_3$
CH$_2$OCH$_3$
CH$_2$OCH$_2$CH$_3$
CH$_2$CO$_2$CH$_3$
CH$_2$CO$_2$CH$_2$CH$_3$
OCH$_2$OCH$_3$
OCH$_2$OCH$_2$CH$_3$
Ph
CH$_2$Ph
OPh
NHPh
COPh
COCH$_2$Ph

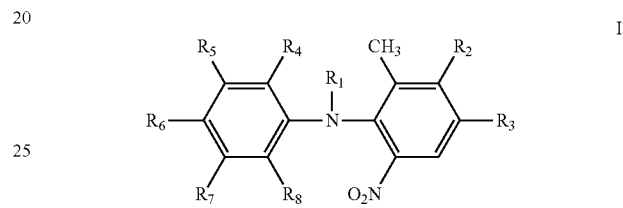

The present invention is also explained by the following compounds in Table 6, but without being restricted thereby.

I

TABLE 6

| No. | $R_1$ | $R_2$ | $R_3$ | $R_4$ | $R_5$ | $R_6$ | $R_7$ | $R_8$ |
|---|---|---|---|---|---|---|---|---|
| 1 | H | Cl | NO$_2$ | F | H | F | H | H |
| 2 | H | Cl | NO$_2$ | Cl | H | Cl | H | H |
| 3 | H | Cl | NO$_2$ | Cl | Cl | Cl | H | H |
| 4 | H | Cl | NO$_2$ | Cl | H | Cl | Cl | H |
| 5 | H | Cl | NO$_2$ | Cl | H | Cl | H | Cl |
| 6 | H | Cl | NO$_2$ | CN | H | H | H | H |
| 7 | H | Cl | NO$_2$ | H | H | CN | H | H |
| 8 | H | Cl | NO$_2$ | H | H | NO$_2$ | H | H |
| 9 | H | Cl | NO$_2$ | NO$_2$ | H | NO$_2$ | H | H |
| 10 | H | Cl | NO$_2$ | NO$_2$ | H | NO$_2$ | H | NO$_2$ |
| 11 | H | Cl | NO$_2$ | CF$_3$ | H | H | H | H |
| 12 | H | Cl | NO$_2$ | H | H | CF$_3$ | H | H |
| 13 | H | Cl | NO$_2$ | OCH$_3$ | H | H | H | H |
| 14 | H | Cl | NO$_2$ | H | H | OCH$_3$ | H | H |
| 15 | H | Cl | NO$_2$ | SCH$_3$ | H | H | H | H |
| 16 | H | Cl | NO$_2$ | H | H | SCH$_3$ | H | H |
| 17 | H | Cl | NO$_2$ | OCF$_3$ | H | H | H | H |
| 18 | H | Cl | NO$_2$ | H | H | OCF$_3$ | H | H |
| 19 | H | Cl | NO$_2$ | COCH$_3$ | H | H | H | H |
| 20 | H | Cl | NO$_2$ | H | H | COCH$_3$ | H | H |
| 21 | H | Cl | NO$_2$ | SO$_2$CH$_3$ | H | H | H | H |
| 22 | H | Cl | NO$_2$ | H | H | SO$_2$CH$_3$ | H | H |
| 23 | H | Cl | NO$_2$ | CO$_2$CH$_3$ | H | H | H | H |
| 24 | H | Cl | NO$_2$ | H | H | CO$_2$CH$_3$ | H | H |
| 25 | H | Cl | NO$_2$ | CONHPh | H | H | H | H |
| 26 | H | Cl | NO$_2$ | H | CONHPh | H | H | H |
| 27 | H | Cl | NO$_2$ | H | H | CONHPh | H | H |
| 28 | H | Cl | NO$_2$ | CO$_2$Ph | H | H | H | H |
| 29 | H | Cl | NO$_2$ | CONH$_2$ | H | H | H | H |
| 30 | H | Cl | NO$_2$ | H | H | CONH$_2$ | H | H |
| 31 | H | Cl | NO$_2$ | Cl | H | CF$_3$ | H | H |
| 32 | H | Cl | NO$_2$ | Cl | H | NO$_2$ | H | H |
| 33 | H | Cl | NO$_2$ | Cl | H | CN | H | H |
| 34 | H | Cl | NO$_2$ | CH$_3$ | H | Cl | H | H |
| 35 | H | Cl | NO$_2$ | CF$_3$ | H | Cl | H | H |
| 36 | H | Cl | NO$_2$ | NO$_2$ | H | Cl | H | H |
| 37 | H | Cl | NO$_2$ | CN | H | Cl | H | H |
| 38 | H | Cl | NO$_2$ | Cl | H | Cl | H | NO$_2$ |
| 39 | H | Cl | NO$_2$ | Cl | H | Cl | H | CN |
| 40 | H | Cl | NO$_2$ | Cl | H | Cl | H | CF$_3$ |
| 41 | H | Cl | NO$_2$ | F | H | F | H | NO$_2$ |

TABLE 6-continued

| No. | R₁ | R₂ | R₃ | R₄ | R₅ | R₆ | R₇ | R₈ |
|---|---|---|---|---|---|---|---|---|
| 42 | H | Cl | NO₂ | F | H | NO₂ | H | F |
| 43 | H | Cl | NO₂ | Cl | H | NO₂ | H | Cl |
| 44 | H | Cl | NO₂ | Cl | H | CF₃ | H | Cl |
| 45 | H | Cl | NO₂ | Cl | H | CN | H | Cl |
| 46 | H | Cl | NO₂ | Cl | H | COCH₃ | H | Cl |
| 47 | H | Cl | NO₂ | Cl | H | CONH₂ | H | Cl |
| 48 | H | Cl | NO₂ | NO₂ | H | F | H | H |
| 49 | H | Cl | NO₂ | NO₂ | H | Br | H | H |
| 50 | H | Cl | NO₂ | NO₂ | H | CF₃ | H | H |
| 51 | H | Cl | NO₂ | NO₂ | H | CN | H | H |
| 52 | H | Cl | NO₂ | NO₂ | H | COCH₃ | H | H |
| 53 | H | Cl | NO₂ | NO₂ | H | CONH₂ | H | H |
| 54 | H | Cl | NO₂ | NO₂ | H | CH₃ | H | H |
| 55 | H | Cl | NO₂ | CF₃ | H | NO₂ | H | H |
| 56 | H | Cl | NO₂ | CN | H | NO₂ | H | H |
| 57 | H | Cl | NO₂ | COCH₃ | H | NO₂ | H | H |
| 58 | H | Cl | NO₂ | CONH₂ | H | NO₂ | H | H |
| 59 | H | Cl | NO₂ | CH₃ | H | NO₂ | H | H |
| 60 | H | Cl | NO₂ | Cl | H | F | H | NO₂ |
| 61 | H | Cl | NO₂ | Cl | H | CF₃ | H | NO₂ |
| 62 | H | Cl | NO₂ | Cl | H | NO₂ | H | NO₂ |
| 63 | H | Cl | NO₂ | Cl | H | CN | H | NO₂ |
| 64 | H | Cl | NO₂ | F | H | Cl | H | NO₂ |
| 65 | H | Cl | NO₂ | CH₃ | H | Cl | H | NO₂ |
| 66 | H | Cl | NO₂ | CF₃ | H | Cl | H | NO₂ |
| 67 | H | Cl | NO₂ | NO₂ | H | Cl | H | NO₂ |
| 68 | H | Cl | NO₂ | CN | H | Cl | H | NO₂ |
| 69 | H | Cl | NO₂ | NO₂ | H | CF₃ | H | NO₂ |
| 70 | H | Cl | NO₂ | NO₂ | H | CN | H | NO₂ |
| 71 | H | Cl | NO₂ | NO₂ | H | CH₃ | H | NO₂ |
| 72 | H | Cl | NO₂ | NO₂ | H | F | H | NO₂ |
| 73 | H | Cl | NO₂ | CF₃ | H | NO₂ | H | NO₂ |
| 74 | H | Cl | NO₂ | CN | H | NO₂ | H | NO₂ |
| 75 | H | Cl | NO₂ | CH₃ | H | NO₂ | H | NO₂ |
| 76 | H | Cl | NO₂ | F | H | NO₂ | H | NO₂ |
| 77 | H | Cl | NO₂ | H | CF₃ | CN | H | H |
| 78 | H | Cl | NO₂ | NO₂ | H | CN | CF₃ | H |
| 79 | H | Cl | NO₂ | Br | H | OCF₃ | H | Br |
| 80 | H | Cl | NO₂ | CH₃ | H | Cl | CH₂CO₂C₂H₅ | H |
| 81 | H | Cl | NO₂ | Cl | CH₃ | Cl | H | H |
| 82 | H | Cl | NO₂ | Cl | CH₃ | Cl | H | NO₂ |
| 83 | H | Cl | NO₂ | Cl | CH₃ | H | H | H |
| 84 | H | Cl | NO₂ | CH₃ | Cl | H | H | H |
| 85 | H | Cl | NO₂ | CH₃ | Cl | NO₂ | H | NO₂ |
| 86 | H | Cl | NO₂ | CH₃ | Cl | NO₂ | H | H |
| 87 | H | Cl | NO₂ | Cl | CH₃ | NO₂ | H | NO₂ |
| 88 | H | Cl | NO₂ | Br | H | NO₂ | H | CN |
| 89 | H | Cl | NO₂ | NO₂ | Cl | CF₃ | H | NO₂ |
| 90 | H | Cl | NO₂ | NO₂ | H | Cl | Cl | H |
| 91 | H | Cl | NO₂ | Cl | H | NO₂ | Cl | H |
| 92 | H | Cl | NO₂ | Cl | H | H | Cl | NO₂ |
| 93 | H | Cl | NO₂ | Cl | Cl | NO₂ | H | H |
| 94 | H | Cl | NO₂ | Cl | Cl | H | H | NO₂ |
| 95 | H | Cl | NO₂ | NO₂ | Cl | Cl | H | NO₂ |
| 96 | H | Cl | NO₂ | Cl | H | NO₂ | Cl | NO₂ |
| 97 | H | Cl | NO₂ | Cl | H | Cl | Cl | NO₂ |
| 98 | H | Cl | NO₂ | Cl | Cl | Cl | NO₂ | H |
| 99 | H | Cl | NO₂ | Cl | Cl | Cl | H | NO₂ |
| 100 | H | Cl | NO₂ | Cl | Cl | NO₂ | Cl | NO₂ |
| 101 | H | Cl | NO₂ | Cl | H | OCF₂CHFCF₃ | Cl | H |
| 102 | H | Cl | NO₂ | H | Cl | ![3-chloro-5-(trifluoromethyl)pyridin-2-yloxy] | Cl | H |
| 103 | H | Cl | H | F | H | F | H | H |
| 104 | H | Cl | H | Cl | H | Cl | H | H |
| 105 | H | Cl | H | Cl | Cl | Cl | H | H |
| 106 | H | Cl | H | Cl | H | Cl | Cl | H |
| 107 | H | Cl | H | Cl | H | Cl | H | Cl |
| 108 | H | Cl | H | CN | H | H | H | H |
| 109 | H | Cl | H | H | H | CN | H | H |
| 110 | H | Cl | H | H | H | NO₂ | H | H |

TABLE 6-continued

| No. | R$_1$ | R$_2$ | R$_3$ | R$_4$ | R$_5$ | R$_6$ | R$_7$ | R$_8$ |
|---|---|---|---|---|---|---|---|---|
| 111 | H | Cl | H | NO$_2$ | H | NO$_2$ | H | H |
| 112 | H | Cl | H | NO$_2$ | H | NO$_2$ | H | NO$_2$ |
| 113 | H | Cl | H | H | H | CF$_3$ | H | H |
| 114 | H | Cl | H | Cl | H | NO$_2$ | H | H |
| 115 | H | Cl | H | Cl | H | CN | H | H |
| 116 | H | Cl | H | CH$_3$ | H | Cl | H | H |
| 117 | H | Cl | H | NO$_2$ | H | Cl | H | H |
| 118 | H | Cl | H | CN | H | Cl | H | H |
| 119 | H | Cl | H | Cl | H | NO$_2$ | H | Cl |
| 120 | H | Cl | H | Cl | H | CF$_3$ | H | Cl |
| 121 | H | Cl | H | Cl | H | CN | H | Cl |
| 122 | H | Cl | H | Cl | H | Cl | H | NO$_2$ |
| 123 | H | Cl | H | Cl | H | Cl | H | CN |
| 124 | H | Cl | H | Cl | H | Cl | H | CF$_3$ |
| 125 | H | Cl | H | F | H | F | H | NO$_2$ |
| 126 | H | Cl | H | NO$_2$ | H | CN | H | H |
| 127 | H | Cl | H | Cl | H | CF$_3$ | H | NO$_2$ |
| 128 | H | Cl | H | Cl | H | NO$_2$ | H | NO$_2$ |
| 129 | H | Cl | H | Cl | H | CN | H | NO$_2$ |
| 130 | H | Cl | H | CH$_3$ | H | Cl | H | NO$_2$ |
| 131 | H | Cl | H | NO$_2$ | H | Cl | H | NO$_2$ |
| 132 | H | Cl | H | NO$_2$ | H | CF$_3$ | H | NO$_2$ |
| 133 | H | Cl | H | NO$_2$ | H | CN | H | NO$_2$ |
| 134 | H | Cl | H | CF$_3$ | H | NO$_2$ | H | NO$_2$ |
| 135 | H | Cl | H | CH$_3$ | H | NO$_2$ | H | NO$_2$ |
| 136 | H | Cl | H | H | CF$_3$ | CN | H | H |
| 137 | H | Cl | H | NO$_2$ | H | CN | CF$_3$ | H |
| 138 | H | Cl | H | Br | H | OCF$_3$ | H | Br |
| 139 | H | Cl | H | CH$_3$ | H | Cl | CH$_2$CO$_2$C$_2$H$_5$ | H |
| 140 | H | Cl | H | Cl | CH$_3$ | Cl | H | H |
| 141 | H | Cl | H | Cl | CH$_3$ | Cl | H | NO$_2$ |
| 142 | H | Cl | H | Cl | CH$_3$ | H | H | H |
| 143 | H | Cl | H | CH$_3$ | Cl | H | H | H |
| 144 | H | Cl | H | CH$_3$ | Cl | NO$_2$ | H | H |
| 145 | H | Cl | H | Br | H | NO$_2$ | H | CN |
| 146 | H | Cl | H | NO$_2$ | Cl | CF$_3$ | H | NO$_2$ |
| 147 | H | Cl | H | NO$_2$ | H | Cl | Cl | H |
| 148 | H | Cl | H | Cl | H | NO$_2$ | Cl | H |
| 149 | H | Cl | H | NO$_2$ | Cl | Cl | H | NO$_2$ |
| 150 | H | Cl | H | Cl | H | NO$_2$ | Cl | NO$_2$ |
| 151 | H | Cl | H | Cl | H | Cl | Cl | NO$_2$ |
| 152 | H | Cl | H | Cl | Cl | CN | Cl | CN |
| 153 | H | Cl | H | Cl | H | OCF$_2$OCF$_3$ | Cl | H |
| 154 | H | Cl | CN | Cl | H | NO$_2$ | H | Cl |
| 155 | H | Cl | CN | Cl | H | CF$_3$ | H | Cl |
| 156 | H | Cl | CN | Cl | H | CN | H | Cl |
| 157 | H | Cl | CN | NO$_2$ | H | CF$_3$ | H | NO$_2$ |
| 158 | H | Cl | CN | Cl | H | Cl | H | Cl |
| 159 | H | Cl | CN | NO$_2$ | H | Cl | H | NO$_2$ |
| 160 | H | Cl | CN | Br | H | NO$_2$ | H | CN |
| 161 | H | Cl | CN | NO$_2$ | H | CN | CF$_3$ | H |
| 162 | H | Cl | CN | Cl | H | NO$_2$ | Cl | H |
| 163 | H | Cl | CN | Cl | H | NO$_2$ | Cl | NO$_2$ |
| 164 | H | Cl | CN | Cl | H | Cl | Cl | NO$_2$ |
| 165 | H | Cl | CN | NO$_2$ | H | NO$_2$ | H | H |
| 166 | H | Cl | CN | Cl | H | NO$_2$ | H | NO$_2$ |
| 167 | H | Cl | CN | Cl | H | CN | H | NO$_2$ |
| 168 | H | Cl | CN | Cl | H | Cl | H | NO$_2$ |
| 169 | H | Cl | CN | Cl | H | Cl | H | CN |
| 170 | H | Cl | CN | Cl | H | Cl | H | CF$_3$ |
| 171 | H | Cl | Cl | Cl | H | NO$_2$ | H | Cl |
| 172 | H | Cl | Cl | Cl | H | CF$_3$ | H | Cl |
| 173 | H | Cl | Cl | Cl | H | CN | H | Cl |
| 174 | H | Cl | Cl | NO$_2$ | H | CF$_3$ | H | NO$_2$ |
| 175 | H | Cl | Cl | Cl | H | Cl | H | Cl |
| 176 | H | Cl | Cl | NO$_2$ | H | Cl | H | NO$_2$ |
| 177 | H | Cl | Cl | Br | H | NO$_2$ | H | CN |
| 178 | H | Cl | Cl | NO$_2$ | H | CN | CF$_3$ | H |
| 179 | H | Cl | Cl | Cl | H | NO$_2$ | Cl | H |
| 180 | H | Cl | Cl | Cl | H | NO$_2$ | Cl | NO$_2$ |
| 181 | H | Cl | Cl | Cl | H | Cl | Cl | NO$_2$ |
| 182 | H | Cl | Cl | NO$_2$ | H | NO$_2$ | H | H |
| 183 | H | Cl | Cl | Cl | H | NO$_2$ | H | NO$_2$ |
| 184 | H | Cl | Cl | Cl | H | CN | H | NO$_2$ |
| 185 | H | Cl | Cl | Cl | H | Cl | H | NO$_2$ |
| 186 | H | Cl | Cl | Cl | H | Cl | H | CN |
| 187 | H | Cl | Cl | Cl | H | Cl | H | CF$_3$ |

TABLE 6-continued

| No. | R$_1$ | R$_2$ | R$_3$ | R$_4$ | R$_5$ | R$_6$ | R$_7$ | R$_8$ |
|---|---|---|---|---|---|---|---|---|
| 188 | H | Cl | C(=O)NH$_2$ | Cl | H | NO$_2$ | H | Cl |
| 189 | H | Cl | C(=O)NH$_2$ | Cl | H | CF$_3$ | H | Cl |
| 190 | H | Cl | C(=O)NH$_2$ | Cl | H | CN | H | Cl |
| 191 | H | Cl | C(=O)NH$_2$ | NO$_2$ | H | CF$_3$ | H | NO$_2$ |
| 192 | H | Cl | C(=O)NH$_2$ | Cl | H | Cl | H | Cl |
| 193 | H | Cl | C(=O)NH$_2$ | NO$_2$ | H | Cl | H | NO$_2$ |
| 194 | H | Cl | C(=O)NH$_2$ | Br | H | NO$_2$ | H | CN |
| 195 | H | Cl | C(=O)NH$_2$ | NO$_2$ | H | CN | CF$_3$ | H |
| 196 | H | Cl | C(=O)NH$_2$ | Cl | H | NO$_2$ | Cl | H |
| 197 | H | Cl | C(=O)NH$_2$ | Cl | H | NO$_2$ | Cl | NO$_2$ |
| 198 | H | Cl | C(=O)NH$_2$ | Cl | H | Cl | Cl | NO$_2$ |
| 199 | H | Cl | C(=O)NH$_2$ | NO$_2$ | H | NO$_2$ | H | H |
| 200 | H | Cl | C(=O)NH$_2$ | Cl | H | NO$_2$ | H | NO$_2$ |
| 201 | H | Cl | C(=O)NH$_2$ | Cl | H | CN | H | NO$_2$ |
| 202 | H | Cl | C(=O)NH$_2$ | Cl | H | Cl | H | NO$_2$ |
| 203 | H | Cl | C(=O)NH$_2$ | Cl | H | Cl | H | CN |
| 204 | H | Cl | C(=O)NH$_2$ | Cl | H | Cl | H | CF$_3$ |
| 205 | H | Cl | C(=S)NH$_2$ | Cl | H | NO$_2$ | H | Cl |
| 206 | H | Cl | C(=S)NH$_2$ | Cl | H | CF$_3$ | H | Cl |
| 207 | H | Cl | C(=S)NH$_2$ | Cl | H | CN | H | Cl |
| 208 | H | Cl | C(=S)NH$_2$ | NO$_2$ | H | CF$_3$ | H | NO$_2$ |
| 209 | H | Cl | C(=S)NH$_2$ | Cl | H | Cl | H | Cl |
| 210 | H | Cl | C(=S)NH$_2$ | NO$_2$ | H | Cl | H | NO$_2$ |
| 211 | H | Cl | C(=S)NH$_2$ | Br | H | NO$_2$ | H | CN |
| 212 | H | Cl | C(=S)NH$_2$ | NO$_2$ | H | CN | CF$_3$ | H |
| 213 | H | Cl | C(=S)NH$_2$ | Cl | H | NO$_2$ | Cl | H |
| 214 | H | Cl | C(=S)NH$_2$ | Cl | H | NO$_2$ | Cl | NO$_2$ |
| 215 | H | Cl | C(=S)NH$_2$ | Cl | H | Cl | Cl | NO$_2$ |
| 216 | H | Cl | C(=S)NH$_2$ | NO$_2$ | H | NO$_2$ | H | H |
| 217 | H | Cl | C(=S)NH$_2$ | Cl | H | NO$_2$ | H | NO$_2$ |
| 218 | H | Cl | C(=S)NH$_2$ | Cl | H | CN | H | NO$_2$ |
| 219 | H | Cl | C(=S)NH$_2$ | Cl | H | Cl | H | NO$_2$ |
| 220 | H | Cl | C(=S)NH$_2$ | Cl | H | Cl | H | CN |
| 221 | H | Cl | C(=S)NH$_2$ | Cl | H | Cl | H | CF$_3$ |
| 222 | H | Cl | CO$_2$CH$_3$ | Cl | H | NO$_2$ | H | Cl |
| 223 | H | Cl | CO$_2$CH$_3$ | Cl | H | CF$_3$ | H | Cl |
| 224 | H | Cl | CO$_2$CH$_3$ | Cl | H | CN | H | Cl |
| 225 | H | Cl | CO$_2$CH$_3$ | NO$_2$ | H | CF$_3$ | H | NO$_2$ |
| 226 | H | Cl | CO$_2$CH$_3$ | Cl | H | Cl | H | Cl |
| 227 | H | Cl | CO$_2$CH$_3$ | NO$_2$ | H | Cl | H | NO$_2$ |
| 228 | H | Cl | CO$_2$CH$_3$ | Br | H | NO$_2$ | H | CN |
| 229 | H | Cl | CO$_2$CH$_3$ | NO$_2$ | H | CN | CF$_3$ | H |
| 230 | H | Cl | CO$_2$CH$_3$ | Cl | H | NO$_2$ | Cl | H |
| 231 | H | Cl | CO$_2$CH$_3$ | Cl | H | NO$_2$ | Cl | NO$_2$ |
| 232 | H | Cl | CO$_2$CH$_3$ | Cl | H | Cl | Cl | NO$_2$ |
| 233 | H | Cl | CO$_2$CH$_3$ | NO$_2$ | H | NO$_2$ | H | H |
| 234 | H | Cl | CO$_2$CH$_3$ | Cl | H | NO$_2$ | H | NO$_2$ |
| 235 | H | Cl | CO$_2$CH$_3$ | Cl | H | CN | H | NO$_2$ |
| 236 | H | Cl | CO$_2$CH$_3$ | Cl | H | Cl | H | NO$_2$ |
| 237 | H | Cl | CO$_2$CH$_3$ | Cl | H | Cl | H | CN |
| 238 | H | Cl | CO$_2$CH$_3$ | Cl | H | Cl | H | CF$_3$ |
| 239 | H | Cl | CF$_3$ | Cl | H | NO$_2$ | H | Cl |
| 240 | H | Cl | CF$_3$ | Cl | H | CF$_3$ | H | Cl |
| 241 | H | Cl | CF$_3$ | Cl | H | CN | H | Cl |
| 242 | H | Cl | CF$_3$ | NO$_2$ | H | CF$_3$ | H | NO$_2$ |
| 243 | H | Cl | CF$_3$ | Cl | H | Cl | H | Cl |
| 244 | H | Cl | CF$_3$ | NO$_2$ | H | Cl | H | NO$_2$ |
| 245 | H | Cl | CF$_3$ | Br | H | NO$_2$ | H | CN |
| 246 | H | Cl | CF$_3$ | NO$_2$ | H | CN | CF$_3$ | H |
| 247 | H | Cl | CF$_3$ | Cl | H | NO$_2$ | Cl | H |
| 248 | H | Cl | CF$_3$ | Cl | H | NO$_2$ | Cl | NO$_2$ |
| 249 | H | Cl | CF$_3$ | Cl | H | Cl | Cl | NO$_2$ |
| 250 | H | Cl | CF$_3$ | NO$_2$ | H | NO$_2$ | H | H |
| 251 | H | Cl | CF$_3$ | Cl | H | NO$_2$ | H | NO$_2$ |
| 252 | H | Cl | CF$_3$ | Cl | H | CN | H | NO$_2$ |
| 253 | H | Cl | CF$_3$ | Cl | H | Cl | H | NO$_2$ |
| 254 | H | Cl | CF$_3$ | Cl | H | Cl | H | CN |
| 255 | H | Cl | CF$_3$ | Cl | H | Cl | H | CF$_3$ |
| 256 | H | Cl | SO$_2$CH$_3$ | Cl | H | NO$_2$ | H | Cl |
| 257 | H | Cl | SO$_2$CH$_3$ | Cl | H | CF$_3$ | H | Cl |
| 258 | H | Cl | SO$_2$CH$_3$ | Cl | H | CN | H | Cl |
| 259 | H | Cl | SO$_2$CH$_3$ | NO$_2$ | H | CF$_3$ | H | NO$_2$ |
| 260 | H | Cl | SO$_2$CH$_3$ | Cl | H | Cl | H | Cl |
| 261 | H | Cl | SO$_2$CH$_3$ | NO$_2$ | H | Cl | H | NO$_2$ |
| 262 | H | Cl | SO$_2$CH$_3$ | Br | H | NO$_2$ | H | CN |
| 263 | H | Cl | SO$_2$CH$_3$ | NO$_2$ | H | CN | CF$_3$ | H |
| 264 | H | Cl | SO$_2$CH$_3$ | Cl | H | NO$_2$ | Cl | H |
| 265 | H | Cl | SO$_2$CH$_3$ | Cl | H | NO$_2$ | Cl | NO$_2$ |

TABLE 6-continued

| No. | R₁ | R₂ | R₃ | R₄ | R₅ | R₆ | R₇ | R₈ |
|---|---|---|---|---|---|---|---|---|
| 266 | H | Cl | SO₂CH₃ | Cl | H | Cl | Cl | NO₂ |
| 267 | H | Cl | SO₂CH₃ | NO₂ | H | NO₂ | H | H |
| 268 | H | Cl | SO₂CH₃ | Cl | H | NO₂ | H | NO₂ |
| 269 | H | Cl | SO₂CH₃ | Cl | H | CN | H | NO₂ |
| 270 | H | Cl | SO₂CH₃ | Cl | H | Cl | H | NO₂ |
| 271 | H | Cl | SO₂CH₃ | Cl | H | Cl | H | CN |
| 272 | H | Cl | SO₂CH₃ | Cl | H | Cl | H | CF₃ |
| 273 | CH₃ | Cl | NO₂ | Cl | H | NO₂ | H | Cl |
| 274 | CH₃ | Cl | NO₂ | Cl | H | CF₃ | H | Cl |
| 275 | CH₃ | Cl | NO₂ | Cl | H | CN | H | Cl |
| 276 | CH₃ | Cl | NO₂ | NO₂ | H | CF₃ | H | NO₂ |
| 277 | CH₃ | Cl | NO₂ | Cl | H | Cl | H | Cl |
| 278 | CH₃ | Cl | NO₂ | NO₂ | H | Cl | H | NO₂ |
| 279 | CH₃ | Cl | NO₂ | Br | H | NO₂ | H | CN |
| 280 | CH₃ | Cl | NO₂ | NO₂ | H | CN | CF₃ | H |
| 281 | CH₃ | Cl | NO₂ | Cl | H | NO₂ | Cl | H |
| 282 | CH₃ | Cl | NO₂ | Cl | H | NO₂ | Cl | NO₂ |
| 283 | CH₃ | Cl | NO₂ | Cl | H | Cl | Cl | NO₂ |
| 284 | CH₃ | Cl | NO₂ | NO₂ | H | NO₂ | H | H |
| 285 | CH₃ | Cl | NO₂ | Cl | H | Cl | H | H |
| 286 | CH₃ | Cl | NO₂ | Cl | H | NO₂ | H | NO₂ |
| 287 | CH₃ | Cl | NO₂ | Cl | H | CN | H | NO₂ |
| 288 | CH₃ | Cl | NO₂ | Cl | H | Cl | H | NO₂ |
| 289 | CH₃ | Cl | NO₂ | Cl | H | Cl | H | CN |
| 290 | CH₃ | Cl | NO₂ | Cl | H | Cl | H | CF₃ |
| 291 | CH₃ | Cl | NO₂ | Br | H | NO₂ | H | Br |
| 292 | CH₃ | Cl | NO₂ | F | H | NO₂ | H | F |
| 293 | CH₃ | Cl | NO₂ | Cl | H | NO₂ | H | Br |
| 294 | CH₃ | Cl | NO₂ | F | H | NO₂ | H | Cl |
| 295 | CH₃ | Cl | NO₂ | F | H | NO₂ | H | Br |
| 296 | COCH₃ | Cl | NO₂ | Cl | H | NO₂ | H | Cl |
| 297 | COCH₃ | Cl | NO₂ | Cl | H | CF₃ | H | Cl |
| 298 | COCH₃ | Cl | NO₂ | Cl | H | CN | H | Cl |
| 299 | COCH₃ | Cl | NO₂ | NO₂ | H | CF₃ | H | NO₂ |
| 300 | COCH₃ | Cl | NO₂ | Cl | H | Cl | H | Cl |
| 301 | COCH₃ | Cl | NO₂ | NO₂ | H | Cl | H | NO₂ |
| 302 | COCH₃ | Cl | NO₂ | Br | H | NO₂ | H | CN |
| 303 | COCH₃ | Cl | NO₂ | NO₂ | H | CN | CF₃ | H |
| 304 | COCH₃ | Cl | NO₂ | Cl | H | NO₂ | Cl | H |
| 305 | COCH₃ | Cl | NO₂ | Cl | H | NO₂ | Cl | NO₂ |
| 306 | COCH₃ | Cl | NO₂ | Cl | H | Cl | Cl | NO₂ |
| 307 | COCH₃ | Cl | NO₂ | NO₂ | H | NO₂ | H | H |
| 308 | COCH₃ | Cl | NO₂ | Cl | H | NO₂ | H | NO₂ |
| 309 | COCH₃ | Cl | NO₂ | Cl | H | CN | H | NO₂ |
| 310 | COCH₃ | Cl | NO₂ | Cl | H | Cl | H | NO₂ |
| 311 | COCH₃ | Cl | NO₂ | Cl | H | Cl | H | CN |
| 312 | COCH₃ | Cl | NO₂ | Cl | H | Cl | H | CF₃ |
| 313 | CO₂CH₃ | Cl | NO₂ | Cl | H | NO₂ | H | Cl |
| 314 | CO₂CH₃ | Cl | NO₂ | Cl | H | CF₃ | H | Cl |
| 315 | CO₂CH₃ | Cl | NO₂ | Cl | H | CN | H | Cl |
| 316 | CO₂CH₃ | Cl | NO₂ | NO₂ | H | CF₃ | H | NO₂ |
| 317 | CO₂CH₃ | Cl | NO₂ | Cl | H | Cl | H | Cl |
| 318 | CO₂CH₃ | Cl | NO₂ | NO₂ | H | Cl | H | NO₂ |
| 319 | CO₂CH₃ | Cl | NO₂ | Br | H | NO₂ | H | CN |
| 320 | CO₂CH₃ | Cl | NO₂ | NO₂ | H | CN | CF₃ | H |
| 321 | CO₂CH₃ | Cl | NO₂ | Cl | H | NO₂ | Cl | H |
| 322 | CO₂CH₃ | Cl | NO₂ | Cl | H | NO₂ | Cl | NO₂ |
| 323 | CO₂CH₃ | Cl | NO₂ | Cl | H | Cl | Cl | NO₂ |
| 324 | CO₂CH₃ | Cl | NO₂ | NO₂ | H | NO₂ | H | H |
| 325 | CO₂CH₃ | Cl | NO₂ | Cl | H | NO₂ | H | NO₂ |
| 326 | CO₂CH₃ | Cl | NO₂ | Cl | H | CN | H | NO₂ |
| 327 | CO₂CH₃ | Cl | NO₂ | Cl | H | Cl | H | NO₂ |
| 328 | CO₂CH₃ | Cl | NO₂ | Cl | H | Cl | H | CN |
| 329 | CO₂CH₃ | Cl | NO₂ | Cl | H | Cl | H | CF₃ |
| 330 | SO₂CH₃ | Cl | NO₂ | Cl | H | NO₂ | H | Cl |
| 331 | SO₂CH₃ | Cl | NO₂ | Cl | H | CF₃ | H | Cl |
| 332 | SO₂CH₃ | Cl | NO₂ | Cl | H | CN | H | Cl |
| 333 | SO₂CH₃ | Cl | NO₂ | NO₂ | H | CF₃ | H | NO₂ |
| 334 | SO₂CH₃ | Cl | NO₂ | Cl | H | Cl | H | Cl |
| 335 | SO₂CH₃ | Cl | NO₂ | NO₂ | H | Cl | H | NO₂ |
| 336 | SO₂CH₃ | Cl | NO₂ | Br | H | NO₂ | H | CN |
| 337 | SO₂CH₃ | Cl | NO₂ | NO₂ | H | CN | CF₃ | H |
| 338 | SO₂CH₃ | Cl | NO₂ | Cl | H | NO₂ | Cl | H |
| 339 | SO₂CH₃ | Cl | NO₂ | Cl | H | NO₂ | Cl | NO₂ |
| 340 | SO₂CH₃ | Cl | NO₂ | Cl | H | Cl | Cl | NO₂ |
| 341 | SO₂CH₃ | Cl | NO₂ | NO₂ | H | NO₂ | H | H |
| 342 | SO₂CH₃ | Cl | NO₂ | Cl | H | NO₂ | H | NO₂ |
| 343 | SO₂CH₃ | Cl | NO₂ | Cl | H | CN | H | NO₂ |

TABLE 6-continued

| No. | $R_1$ | $R_2$ | $R_3$ | $R_4$ | $R_5$ | $R_6$ | $R_7$ | $R_8$ |
|---|---|---|---|---|---|---|---|---|
| 344 | $SO_2CH_3$ | Cl | $NO_2$ | Cl | H | Cl | H | $NO_2$ |
| 345 | $SO_2CH_3$ | Cl | $NO_2$ | Cl | H | Cl | H | CN |
| 346 | $SO_2CH_3$ | Cl | $NO_2$ | Cl | H | Cl | H | $CF_3$ |
| 347 | H | $OCH_3$ | $NO_2$ | Cl | H | $NO_2$ | H | Cl |
| 348 | H | $OCH_3$ | $NO_2$ | Cl | H | $CF_3$ | H | Cl |
| 349 | H | $OCH_3$ | $NO_2$ | Cl | H | CN | H | Cl |
| 350 | H | $OCH_3$ | $NO_2$ | $NO_2$ | H | $CF_3$ | H | $NO_2$ |
| 351 | H | $OCH_3$ | $NO_2$ | Cl | H | Cl | H | Cl |
| 352 | H | $OCH_3$ | $NO_2$ | $NO_2$ | H | Cl | H | $NO_2$ |
| 353 | H | $OCH_3$ | $NO_2$ | Br | H | $NO_2$ | H | CN |
| 354 | H | $OCH_3$ | $NO_2$ | $NO_2$ | H | CN | $CF_3$ | H |
| 355 | H | $OCH_3$ | $NO_2$ | Cl | H | $NO_2$ | Cl | H |
| 356 | H | $OCH_3$ | $NO_2$ | Cl | H | $NO_2$ | Cl | $NO_2$ |
| 357 | H | $OCH_3$ | $NO_2$ | Cl | H | Cl | Cl | $NO_2$ |
| 358 | H | $OCH_3$ | $NO_2$ | $NO_2$ | H | $NO_2$ | H | H |
| 359 | H | $OCH_3$ | $NO_2$ | Cl | H | $NO_2$ | H | $NO_2$ |
| 360 | H | $OCH_3$ | $NO_2$ | Cl | H | CN | H | $NO_2$ |
| 361 | H | $OCH_3$ | $NO_2$ | Cl | H | Cl | H | $NO_2$ |
| 362 | H | $OCH_3$ | $NO_2$ | Cl | H | Cl | H | CN |
| 363 | H | $OCH_3$ | $NO_2$ | Cl | H | Cl | H | $CF_3$ |
| 364 | H | $OCH_3$ | $NO_2$ | Br | H | $NO_2$ | H | Br |
| 365 | H | $OCH_3$ | $NO_2$ | F | H | $NO_2$ | H | F |
| 366 | H | $OCH_3$ | $NO_2$ | Cl | H | $NO_2$ | H | Br |
| 367 | H | $OCH_3$ | $NO_2$ | F | H | $NO_2$ | H | Cl |
| 368 | H | $OCH_3$ | $NO_2$ | F | H | $NO_2$ | H | Br |
| 369 | H | $SCH_3$ | $NO_2$ | Cl | H | $NO_2$ | H | Cl |
| 370 | H | $SCH_3$ | $NO_2$ | Cl | H | $CF_3$ | H | Cl |
| 371 | H | $SCH_3$ | $NO_2$ | Cl | H | CN | H | Cl |
| 372 | H | $SCH_3$ | $NO_2$ | $NO_2$ | H | $CF_3$ | H | $NO_2$ |
| 373 | H | $SCH_3$ | $NO_2$ | Cl | H | Cl | H | Cl |
| 374 | H | $SCH_3$ | $NO_2$ | $NO_2$ | H | Cl | H | $NO_2$ |
| 375 | H | $SCH_3$ | $NO_2$ | Br | H | $NO_2$ | H | CN |
| 376 | H | $SCH_3$ | $NO_2$ | $NO_2$ | H | CN | $CF_3$ | H |
| 377 | H | $SCH_3$ | $NO_2$ | Cl | H | $NO_2$ | Cl | H |
| 378 | H | $SCH_3$ | $NO_2$ | Cl | H | $NO_2$ | Cl | $NO_2$ |
| 379 | H | $SCH_3$ | $NO_2$ | Cl | H | Cl | Cl | $NO_2$ |
| 380 | H | $SCH_3$ | $NO_2$ | $NO_2$ | H | $NO_2$ | H | H |
| 381 | H | $SCH_3$ | $NO_2$ | Cl | H | $NO_2$ | H | $NO_2$ |
| 382 | H | $SCH_3$ | $NO_2$ | Cl | H | CN | H | $NO_2$ |
| 383 | H | $SCH_3$ | $NO_2$ | Cl | H | Cl | H | $NO_2$ |
| 384 | H | $SCH_3$ | $NO_2$ | Cl | H | Cl | H | CN |
| 385 | H | $SCH_3$ | $NO_2$ | Cl | H | Cl | H | $CF_3$ |
| 386 | H | $SCH_3$ | $NO_2$ | Br | H | $NO_2$ | H | Br |
| 387 | H | $SCH_3$ | $NO_2$ | F | H | $NO_2$ | H | F |
| 388 | H | $SCH_3$ | $NO_2$ | Cl | H | $NO_2$ | H | Br |
| 389 | H | $SCH_3$ | $NO_2$ | F | H | $NO_2$ | H | Cl |
| 390 | H | $SCH_3$ | $NO_2$ | F | H | $NO_2$ | H | Br |
| 391 | H | $NHCH_3$ | $NO_2$ | Cl | H | $NO_2$ | H | Cl |
| 392 | H | $NHCH_3$ | $NO_2$ | Cl | H | $CF_3$ | H | Cl |
| 393 | H | $NHCH_3$ | $NO_2$ | Cl | H | CN | H | Cl |
| 394 | H | $NHCH_3$ | $NO_2$ | $NO_2$ | H | $CF_3$ | H | $NO_2$ |
| 395 | H | $NHCH_3$ | $NO_2$ | Cl | H | Cl | H | Cl |
| 396 | H | $NHCH_3$ | $NO_2$ | $NO_2$ | H | Cl | H | $NO_2$ |
| 397 | H | $NHCH_3$ | $NO_2$ | Br | H | $NO_2$ | H | CN |
| 398 | H | $NHCH_3$ | $NO_2$ | $NO_2$ | H | CN | $CF_3$ | H |
| 399 | H | $NHCH_3$ | $NO_2$ | Cl | H | $NO_2$ | Cl | H |
| 400 | H | $NHCH_3$ | $NO_2$ | Cl | H | $NO_2$ | Cl | $NO_2$ |
| 401 | H | $NHCH_3$ | $NO_2$ | Cl | H | Cl | Cl | $NO_2$ |
| 402 | H | $NHCH_3$ | $NO_2$ | $NO_2$ | H | $NO_2$ | H | H |
| 403 | H | $NHCH_3$ | $NO_2$ | Cl | H | $NO_2$ | H | $NO_2$ |
| 404 | H | $NHCH_3$ | $NO_2$ | Cl | H | CN | H | $NO_2$ |
| 405 | H | $NHCH_3$ | $NO_2$ | Cl | H | Cl | H | $NO_2$ |
| 406 | H | $NHCH_3$ | $NO_2$ | Cl | H | Cl | H | CN |
| 407 | H | $NHCH_3$ | $NO_2$ | Cl | H | Cl | H | $CF_3$ |
| 408 | H | $NHCH_3$ | $NO_2$ | Br | H | $NO_2$ | H | Br |
| 409 | H | $NHCH_3$ | $NO_2$ | F | H | $NO_2$ | H | F |
| 410 | H | $NHCH_3$ | $NO_2$ | Cl | H | $NO_2$ | H | Br |
| 411 | H | $NHCH_3$ | $NO_2$ | F | H | $NO_2$ | H | Cl |
| 412 | H | $NHCH_3$ | $NO_2$ | F | H | $NO_2$ | H | Br |
| 413 | H | $N(CH_3)_2$ | $NO_2$ | Cl | H | $NO_2$ | H | Cl |
| 414 | H | $N(CH_3)_2$ | $NO_2$ | Cl | H | $CF_3$ | H | Cl |
| 415 | H | $N(CH_3)_2$ | $NO_2$ | Cl | H | CN | H | Cl |
| 416 | H | $N(CH_3)_2$ | $NO_2$ | $NO_2$ | H | $CF_3$ | H | $NO_2$ |
| 417 | H | $N(CH_3)_2$ | $NO_2$ | Cl | H | Cl | H | Cl |
| 418 | H | $N(CH_3)_2$ | $NO_2$ | $NO_2$ | H | Cl | H | $NO_2$ |
| 419 | H | $N(CH_3)_2$ | $NO_2$ | Br | H | $NO_2$ | H | CN |
| 420 | H | $N(CH_3)_2$ | $NO_2$ | $NO_2$ | H | CN | $CF_3$ | H |
| 421 | H | $N(CH_3)_2$ | $NO_2$ | Cl | H | $NO_2$ | Cl | H |

TABLE 6-continued

| No. | R₁ | R₂ | R₃ | R₄ | R₅ | R₆ | R₇ | R₈ |
|---|---|---|---|---|---|---|---|---|
| 422 | H | N(CH₃)₂ | NO₂ | Cl | H | NO₂ | Cl | NO₂ |
| 423 | H | N(CH₃)₂ | NO₂ | Cl | H | Cl | Cl | NO₂ |
| 424 | H | N(CH₃)₂ | NO₂ | NO₂ | H | NO₂ | H | H |
| 425 | H | N(CH₃)₂ | NO₂ | Cl | H | NO₂ | H | NO₂ |
| 426 | H | N(CH₃)₂ | NO₂ | Cl | H | CN | H | NO₂ |
| 427 | H | N(CH₃)₂ | NO₂ | Cl | H | Cl | H | NO₂ |
| 428 | H | N(CH₃)₂ | NO₂ | Cl | H | Cl | H | CN |
| 429 | H | N(CH₃)₂ | NO₂ | Cl | H | Cl | H | CF₃ |
| 430 | H | N(CH₃)₂ | NO₂ | Br | H | NO₂ | H | Br |
| 431 | H | N(CH₃)₂ | NO₂ | F | H | NO₂ | H | F |
| 432 | H | N(CH₃)₂ | NO₂ | Cl | H | NO₂ | H | Br |
| 433 | H | N(CH₃)₂ | NO₂ | F | H | NO₂ | H | Cl |
| 434 | H | N(CH₃)₂ | NO₂ | F | H | NO₂ | H | Br |
| 435 | H | OPh | NO₂ | Cl | H | NO₂ | H | Cl |
| 436 | H | OPh | NO₂ | Cl | H | CF₃ | H | Cl |
| 437 | H | OPh | NO₂ | Cl | H | CN | H | Cl |
| 438 | H | OPh | NO₂ | NO₂ | H | CF₃ | H | NO₂ |
| 439 | H | OPh | NO₂ | Cl | H | Cl | H | Cl |
| 440 | H | OPh | NO₂ | NO₂ | H | Cl | H | NO₂ |
| 441 | H | OPh | NO₂ | Br | H | NO₂ | H | CN |
| 442 | H | OPh | NO₂ | NO₂ | H | CN | CF₃ | H |
| 443 | H | OPh | NO₂ | Cl | H | NO₂ | Cl | H |
| 444 | H | OPh | NO₂ | Cl | H | NO₂ | Cl | NO₂ |
| 445 | H | OPh | NO₂ | Cl | H | Cl | Cl | NO₂ |
| 446 | H | OPh | NO₂ | NO₂ | H | NO₂ | H | H |
| 447 | H | OPh | NO₂ | Cl | H | NO₂ | H | NO₂ |
| 448 | H | OPh | NO₂ | Cl | H | CN | H | NO₂ |
| 449 | H | OPh | NO₂ | Cl | H | Cl | H | NO₂ |
| 450 | H | OPh | NO₂ | Cl | H | Cl | H | CN |
| 451 | H | OPh | NO₂ | Cl | H | Cl | H | CF₃ |
| 452 | H | OPh | NO₂ | Br | H | NO₂ | H | Br |
| 453 | H | OPh | NO₂ | F | H | NO₂ | H | F |
| 454 | H | OPh | NO₂ | Cl | H | NO₂ | H | Br |
| 455 | H | OPh | NO₂ | F | H | NO₂ | H | Cl |
| 456 | H | OPh | NO₂ | F | H | NO₂ | H | Br |
| 457 | H | OCH₂CF₃ | NO₂ | Cl | H | NO₂ | H | Cl |
| 458 | H | OCH₂CF₃ | NO₂ | Cl | H | CF₃ | H | Cl |
| 459 | H | OCH₂CF₃ | NO₂ | Cl | H | CN | H | Cl |
| 460 | H | OCH₂CF₃ | NO₂ | NO₂ | H | CF₃ | H | NO₂ |
| 461 | H | OCH₂CF₃ | NO₂ | Cl | H | Cl | H | Cl |
| 462 | H | OCH₂CF₃ | NO₂ | NO₂ | H | Cl | H | NO₂ |
| 463 | H | OCH₂CF₃ | NO₂ | Br | H | NO₂ | H | CN |
| 464 | H | OCH₂CF₃ | NO₂ | NO₂ | H | CN | CF₃ | H |
| 465 | H | OCH₂CF₃ | NO₂ | Cl | H | NO₂ | Cl | H |
| 466 | H | OCH₂CF₃ | NO₂ | Cl | H | NO₂ | Cl | NO₂ |
| 467 | H | OCH₂CF₃ | NO₂ | Cl | H | Cl | Cl | NO₂ |
| 468 | H | OCH₂CF₃ | NO₂ | NO₂ | H | NO₂ | H | H |
| 469 | H | OCH₂CF₃ | NO₂ | Cl | H | NO₂ | H | NO₂ |
| 470 | H | OCH₂CF₃ | NO₂ | Cl | H | CN | H | NO₂ |
| 471 | H | OCH₂CF₃ | NO₂ | Cl | H | Cl | H | NO₂ |
| 472 | H | OCH₂CF₃ | NO₂ | Cl | H | Cl | H | CN |
| 473 | H | OCH₂CF₃ | NO₂ | Cl | H | Cl | H | CF₃ |
| 474 | H | OCH₂CF₃ | NO₂ | Br | H | NO₂ | H | Br |
| 475 | H | OCH₂CF₃ | NO₂ | F | H | NO₂ | H | F |
| 476 | H | OCH₂CF₃ | NO₂ | Cl | H | NO₂ | H | Br |
| 477 | H | OCH₂CF₃ | NO₂ | F | H | NO₂ | H | Cl |
| 478 | H | OCH₂CF₃ | NO₂ | F | H | NO₂ | H | Br |
| 479 | H | NHCH₂CF₃ | NO₂ | Cl | H | NO₂ | H | Cl |
| 480 | H | NHCH₂CF₃ | NO₂ | Cl | H | CF₃ | H | Cl |
| 481 | H | NHCH₂CF₃ | NO₂ | Cl | H | CN | H | Cl |
| 482 | H | NHCH₂CF₃ | NO₂ | NO₂ | H | CF₃ | H | NO₂ |
| 483 | H | NHCH₂CF₃ | NO₂ | Cl | H | Cl | H | Cl |
| 484 | H | NHCH₂CF₃ | NO₂ | NO₂ | H | Cl | H | NO₂ |
| 485 | H | NHCH₂CF₃ | NO₂ | Br | H | NO₂ | H | CN |
| 486 | H | NHCH₂CF₃ | NO₂ | NO₂ | H | CN | CF₃ | H |
| 487 | H | NHCH₂CF₃ | NO₂ | Cl | H | NO₂ | Cl | H |
| 488 | H | NHCH₂CF₃ | NO₂ | Cl | H | NO₂ | Cl | NO₂ |
| 489 | H | NHCH₂CF₃ | NO₂ | Cl | H | Cl | Cl | NO₂ |
| 490 | H | NHCH₂CF₃ | NO₂ | NO₂ | H | NO₂ | H | H |
| 491 | H | NHCH₂CF₃ | NO₂ | Cl | H | NO₂ | H | NO₂ |
| 492 | H | NHCH₂CF₃ | NO₂ | Cl | H | CN | H | NO₂ |
| 493 | H | NHCH₂CF₃ | NO₂ | Cl | H | Cl | H | NO₂ |
| 494 | H | NHCH₂CF₃ | NO₂ | Cl | H | Cl | H | CN |
| 495 | H | NHCH₂CF₃ | NO₂ | Cl | H | Cl | H | CF₃ |
| 496 | H | NHCH₂CF₃ | NO₂ | Br | H | NO₂ | H | Br |
| 497 | H | NHCH₂CF₃ | NO₂ | F | H | NO₂ | H | F |
| 498 | H | NHCH₂CF₃ | NO₂ | Cl | H | NO₂ | H | Br |
| 499 | H | NHCH₂CF₃ | NO₂ | F | H | NO₂ | H | Cl |

TABLE 6-continued

| No. | $R_1$ | $R_2$ | $R_3$ | $R_4$ | $R_5$ | $R_6$ | $R_7$ | $R_8$ |
|---|---|---|---|---|---|---|---|---|
| 500 | H | NHCH$_2$CF$_3$ | NO$_2$ | F | H | NO$_2$ | H | Br |
| 501 | H | Cl | NO$_2$ | Cl | H | NO$_2$ | H | Br |
| 502 | H | Cl | NO$_2$ | Br | H | NO$_2$ | H | Br |
| 503 | H | Cl | NO$_2$ | Cl | H | CO$_2$CH$_3$ | H | Cl |
| 504 | H | Cl | NO$_2$ | F | H | NO$_2$ | H | Cl |
| 505 | H | Cl | NO$_2$ | F | H | H | H | F |
| 506 | H | Cl | NO$_2$ | F | H | Cl | H | F |
| 507 | CH$_3$ | Cl | NO$_2$ | NO$_2$ | H | NO$_2$ | H | NO$_2$ |
| 508 | H | Cl | NO$_2$ | Cl | H | CONHCH$_3$ | H | Cl |
| 509 | H | NHCH$_3$ | NO$_2$ | Cl | H | CONHCH$_3$ | H | Cl |
| 510 | CH$_3$ | Cl | NO$_2$ | Cl | H | CF$_3$ | H | H |
| 511 | H | Cl | NO$_2$ | Cl | H | COOH | H | Cl |
| 512 | CH$_2$CH=CH$_2$ | Cl | NO$_2$ | Cl | H | NO$_2$ | H | Cl |
| 513 | CH$_2$CH=CCl$_2$ | Cl | NO$_2$ | Cl | H | NO$_2$ | H | Cl |
| 514 | CH$_2$CH=CF$_2$ | Cl | NO$_2$ | Cl | H | NO$_2$ | H | Cl |
| 515 | (CH$_2$)$_2$CH=CF$_2$ | Cl | NO$_2$ | Cl | H | NO$_2$ | H | Cl |
| 516 | (CH$_2$)$_2$CF=CF$_2$ | Cl | NO$_2$ | Cl | H | NO$_2$ | H | Cl |
| 517 | CH$_2$CHF$_2$ | Cl | NO$_2$ | Cl | H | NO$_2$ | H | Cl |
| 518 | CH$_2$C≡CH | Cl | NO$_2$ | Cl | H | NO$_2$ | H | Cl |
| 519 | CH$_2$C≡C—I | Cl | NO$_2$ | Cl | H | NO$_2$ | H | Cl |
| 520 | CH$_2$C≡CH$_3$ | Cl | NO$_2$ | Cl | H | NO$_2$ | H | Cl |
| 521 | H | Cl | NO$_2$ | CH$_3$ | H | H | H | Cl |
| 522 | H | Cl | NO$_2$ | CH$_3$ | H | NO$_2$ | H | Cl |
| 523 | H | Cl | NO$_2$ | CH$_3$ | H | NO$_2$ | H | Br |
| 524 | H | Cl | NO$_2$ | CH$_3$ | H | NO$_2$ | H | F |

The technical scheme of the present invention also includes the preparation method of the compounds, and the reaction formula is as follow:

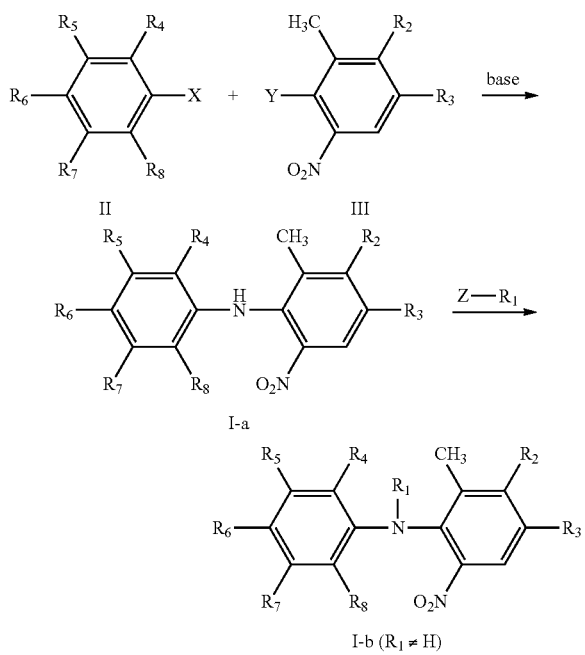

Wherein: X and Y are different, separately selected from halogen atom or amino; Z is halogen atom; $R_2$, $R_3$, $R_4$, $R_5$, $R_6$, $R_7$ and $R_8$ are defined respectively as mentioned before; $R_1$ are defined as mentioned before, but $R_1 \neq H$.

According to the above preparation method, treatment of intermediate II with intermediate III at the presence of base gives compounds I-a of general formula I ($R_1$=H), which react with Z—$R_1$ to give compounds I-b of general formula I ($R_1 \neq H$).

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction can be carried out in proper solvent, and the proper solvent mentioned may be selected from tetrahydrofuran, acetonitrile, toluene, xylene, benzene, DMF, N-methylpyrrolidone, DMSO, acetone or butanone and so on.

The proper reaction temperature is from room temperature to boiling point of solvent, generally is 20-100° C.

The reaction time is in the range of 30 minutes to 20 hours, generally is 1-10 hours.

Intermediates II are commercially available, or prepared according to the known methods, such as referring to Indian Journal of Chemistry, Section B: Organic Chemistry Including Medicinal Chemistry, 45B(4), 972-975, 2006; Tetrahedron Letters, 44(21), 4085-4088, 2003; PL174903, etc.

Intermediate III can be prepared according to the known methods, such as referring to JP2003292476, US2010160695, etc.

The compounds of general formula I can also be prepared by other methods, for example, the nitration of substituted diphenylamine intermediate (general formula IV) can give compounds of general formula I with NO$_2$ group, referring to US4041172 and so on.

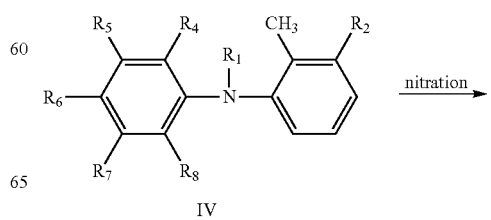

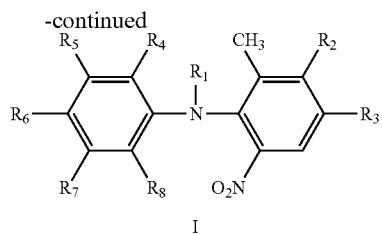

I

Wherein: $R_1$, $R_2$, $R_4$, $R_5$, $R_6$, $R_7$ and $R_8$ are defined respectively as mentioned before; $R_3$ is selected from H or $NO_2$.

The nitration of compounds of general formula I, in which at least one of $R_4$, $R_6$ or $R_8$ is H, can add one or two $NO_2$ groups to these compounds of general formula I.

The halogenation of substituted diphenylamine compounds of general formula I, in which $R_4$, $R_6$ or $R_8$ is not halogen atom, can add one or two halogen atoms to these compounds of general formula I.

The compounds of general formula I, in which $R_2$ is alkylamino, alkoxy or alkylthio and so on, can be prepared from the reaction of compounds of general formula I whose $R_2$ is halogen atom with amine, alcohol or mercaptan (or their salts).

The salts of compounds having general formula I can be prepared from the reaction of the compounds of general formula I with corresponding acid according to routine method. The proper acid may be selected from hydrochloric acid, sulfuric acid, phosphoric acid, trifluoroacetic acid, methylsulfonic acid, p-toluenesulfonic acid, etc.

Although the compounds having general formula I of the present invention and some compounds reported in the prior art are all diphenylamine compounds, there are significant differences between their structural characteristics. And because of the structural differences, the compounds of the present invention show much better fungicidal activity. Meanwhile, the raw materials to prepare these compounds are cheap and the methods are simple and convenient, therefore the compounds of the present invention have lower costs and broader application prospect compared with known fungicides.

The compounds of general formula I show excellent activity against many plant pathogens/diseases in agricultural and other fields. Therefore the technical scheme of the present invention also include the uses of the compounds having general formula I to control plant pathogens/diseases in agricultural and other fields, such as using the compounds of general formula I to prepare substances to control plant pathogens/diseases.

The present invention is explained by the following examples of plant disease, but without being restricted thereby.

The compounds of general formula I can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), pythium rot (pepper soft stale disease, vegetable sponge cottony leak, chinese wax gourd cottony leak), blight (broad bean phytophthora blight, cucumber phytophthora blight, pumpkin phytophthora rot, chinese wax gourd phytophthora blight, watermelon phytophthora blight, muskmelon phytophthora blight, pepper phytophthora blight, chinese chives phytophthora blight, carlic phytophthora blight, cotton phytophthora blight), late blight (potato late blight, tomato late blight) and so on; diseases caused by Deuteromycotina, such as wilt disease (sweet potato fusarium wilt, cotton fusarium wilt disease, sesame wilt disease, fusarium wilt disease of costarbean, tomato fusarium wilt, bean fusarium wilt, cucumber fusarium wilt, vegetable sponge fusarium wilt, pumpkin fusarium wilt, chinese wax gourd fusarium wilt, watermelon fusarium wilt, muskmelon fusarium wilt, pepper fusarium wilt, broad bean fusarium wilt, fusarium wilt disease of rape, fusarium wilt disease of soybean), root rot (pepper root rot, eggplant root rot, bean fusarium root-rot, cucumber fusarium root rot, balsam pear fusarium root rot, cotton black root rot, broad bean thielaviopsis root rot), drooping disease (cotton soreshin, sesame soreshin, pepper rhizoctonia rot, cucumber rhizoctonia rot, chinese cabbage rhizoctonia rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), verticillium wilt (cotton verticillium wilt, verticillium wilt of sunflower, tomato verticillium wilt, pepper verticillium wilt, eggplant verticillium wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd corynespora leaf spot, soybean brown spot, sunflower brown spot, pea ascochyta blight, broad bean brown spot), black spot (flax black spot, rape alternaria leaf spot, sesame black spot, sunflower alternaria leaf spot, costarbean alternaria leaf spot, tomato nail head spot, pepper black fruit spot, eggplant black spot, bean leaf spot, cucumber alternaria blight, celery alternaria black leaf spot, carrot alternaria black rot, carrot leaf blight, apple alternaria rot, peanut brown spot), spot blight (tomato septoria leaf spot, pepper septoria leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon alternaria blight, muskmelon alternaria spot), basal stem rot (tomato basal stem rot, bean rhizoctonia rot), and others (corn northern leaf spot, kenaf damping-off, rice blast, millet black sheath, sugarcane eye spot, cotton aspergillus boll rot, peanut crown rot, soybean stem blight, soybean black spot, muskmelon alternaria leaf blight, peanut web blotch, tea red leaf spot, pepper phyllosticta blight, chinese wax gourd phyllosticta leaf spot, celery black rot, spinach heart rot, kenaf leaf mold, kenaf brown leaf spot, Jute stem blight, soybean cercospora spot, sesame leaf spot, costarbean gray leaf spot, tea brown leaf spot, eggplant cercospora leaf spot, bean cercospora leaf spot, balsam pear cercospora leaf spot, watermelon cercospora leaf spot, jute dry rot, sunflower root and stem rot, bean charcoal rot, soybean target spot, eggplant corynespora leaf spot, cucumber corynespora target leaf spot, tomato leaf mold, eggplant fulvia leaf mold, broad bean chocolate spot) and so on; diseases caused by Basidiomycete, such as rust (wheat stripe rust, wheat stem rust, wheat leaf rust, peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powdery mildew, pumpkin powdery mildew, summer squash powdery mildew, chinese wax gourd, muskmelon powdery mildew, grape powdery mildew, broad bean powdery mildew), sclerotinia rot (flax sclertiniose, rape sclertiniose, soybean sclertiniose, peanut sclertiniose, tobacco sclerotinia rot, pepper sclerotinia rot, eggplant sclerotinia rot, bean sclerotinia rot, pea sclerotinia rot, cucumber sclerotinia rot, balsam pear sclerotinia rot, chinese wax gourd sclerotinia rot, watermelon sclerotinia disease, celery stem rot), scab (apple scab, pear scab) and so on. Especially, the compounds of the present invention exhibit very good control against cucumber downy mildew, rice blast and gray mold of vegetables at very low doses.

Thanks to their positive characteristics, the compounds mentioned above can be advantageously used in protecting crops of farming and gardening, domestic and breeding animals, as well as environments frequented by human beings, from pathogens.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

An another object of the present invention also relates to a method for controlling phytopathogenic fungi in crops of farming and gardening and/or on domestic and breeding animals and/or environments frequented by human beings, by application of the compounds having general formula I. In particular, the dosage of compounds to be applied varies from 10 g to 5 kg per hectare.

For practical application in agriculture, it is usually beneficial to use compositions containing one or more compounds of general formula I.

Therefore, a further technical scheme of the present invention relates to fungicidal compositions containing one or more compounds having general formula I as active ingredient and acceptable carrier in agriculture, the weight percentage of the active ingredient in the compositions is 0.5-90%.

Compositions can be used in the form of dry powders, wettable powders, emulsifiable concentrates, microemulsions, pastes, granulates, solutions, suspensions, etc. The selection of the type of compositions depends on the specific application.

The compositions are prepared in the known method, for example by diluting or dissolving the active substance with a solvent medium and/or a solid diluent, optionally in the presence of surface-active agents.

Solid diluents or carriers which can be used are, for example: silica, kaolin, bentonite, talc, diatomite, dolomite, calcium carbonate, magnesia, chalk, clays, synthetic silicates, attapulgite, sepiolite.

Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N, N-dimethylformamide, N-methylpyrrolidone, etc.).

Surface-active agents which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 1% to 90%, preferably from 5% to 50%.

If required, other active ingredients being compatible with the compounds having general formula I can be added to the compositions, such as, other acaricides/insecticides, fungicides, plant growth regulators, antibiotics, herbicides, fertilizers.

The preparation methods of several common formulation examples in the present invention are as follows:

The preparation of suspension concentrate: the common active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together to make a homogeneous oil phase. The water is mixed with antifreeze to make a homogeneous aqueous phase. In the high-speed stirring, the aqueous phase is added to the oil phase or oil phase is added to the aqueous phase, forming the water emulsion with good dispersity. The active component of water emulsions is generally 5%–15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-40%). To prepare the spraying wettable powder, the compounds of this invention can form a mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation machine with 10 to 100 mesh for granulation, then by drying and sieving (at the scope screen). Also, the compound of the invention, dispersants, disintegrants, wetting agents and solid diluent are added to sanding machine, grinding in water to produce suspension and then spray-drying granulation, usually the content of the prepared granular products is 20%-30%.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

The Preparation of Compound 2

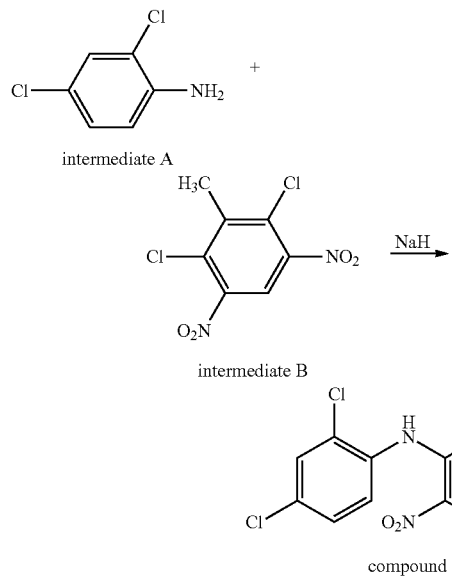

0.81 g (0.005 mol) of 2,4-dichloroaniline was added in portions to a suspension of 0.4 g (0.01 mol) of NaH (60%) and 20 mL of THF, the mixture was stirred for 30 min after addition, 1.56 g (0.006 mol) of 2,6-dichloro-3,5-dinitrotulune in 30 mL of THF was added within 30 min, then stirred for another 5 h. After the reaction was over by Thin-Layer Chromatography monitoring, the reaction mixture was filtered. The filtrate was concentrated under reduced pressure, then the residue was purified through silica column (ethyl acetate/petroleum ether (boiling point range 60-90° C.)=1/20, as an eluent) to give 1.37 g of compound 2 as yellow solid, m.p. 136-137° C.

$^1$H-NMR spectrum (300 MHz, internal standard: TMS, solvent CDCl$_3$) δ (ppm): 2.14 (s, 3H), 6.53 (d, 1H), 7.17 (d, 1H), 7.49 (s, 1H), 8.68 (s, 1H), 8.93 (s, 1H).

Example 2

The Preparation of Compound 38

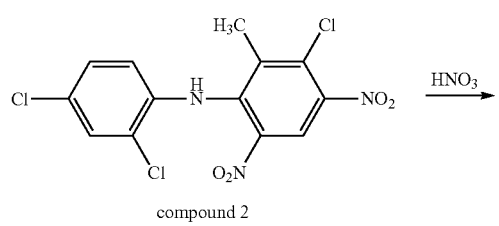

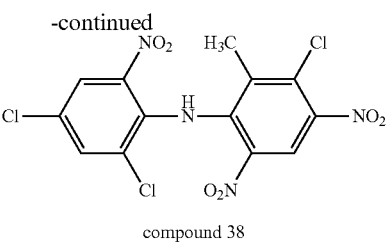

0.56 g (0.0015 mol) of compound 2 was dissolved in 5 mL of concentrated sulfuric acid (96%, the same below) and cooled to 0° C., 0.15 g of fuming nitric acid (95%) and 3 mL of concentrated sulfuric acid was mixed evenly and added to the flask, then the reaction mixture was stirred for another 5 min. After the reaction was over by Thin-Layer Chromatography monitoring, the reaction mixture was poured into ice water, the solid precipitated was filtered, and the filter mass was washed with water and dried to give 0.59 g of compound 38 as brown solid, m.p. 156-158° C.

$^1$H-NMR spectrum (300 MHz, internal standard: TMS, solvent CDCl$_3$) δ (ppm): 2.09 (s, 3H), 7.66 (s, 1H), 8.01 (s, 1H), 8.60 (s, 1H), 9.75 (s, 1H).

Example 3

The Preparation of Compound 43

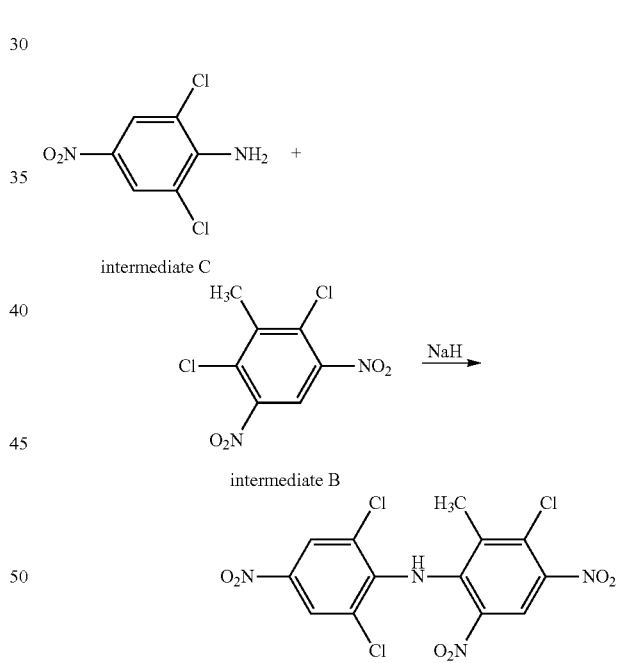

0.83 g (0.004 mol) of 2,6-dichloro-4-nitroaniline was added in portions to a suspension of 0.32 g (0.008 mol) of NaH (60%) and 10 mL of DMF, the mixture was stirred for 30 min after addition, 1.20 g (0.0048 mol) of 2,6-dichloro-3,5-dinitrotulune was added in portions within 30 min, then stirred for another 3 h. After the reaction was over by Thin-Layer Chromatography monitoring, the reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/10, as an eluent) to give 1.20 g of compound 43 as yellow solid, m.p. 157-158° C.

$^1$H-NMR spectrum (300 MHz, internal standard: TMS, solvent CDCl$_3$) δ (ppm): 2.02 (s, 3H), 8.29 (s, 2H), 8.65 (s, 1H), 8.95 (s, 1H).

Example 4

The Preparation of Compound 89

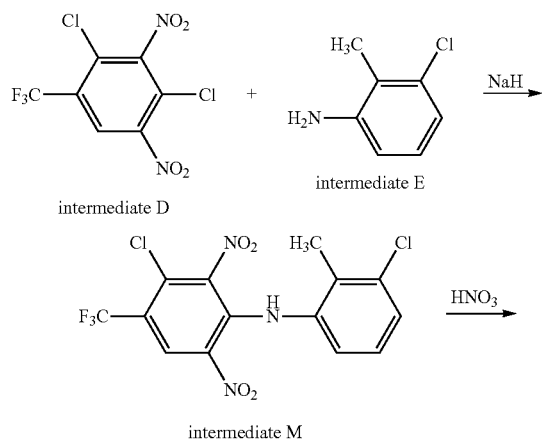

The intermediate M prepared by the procedure of Example 3 was nitrated according to Example 2 to give compound 89 as reddish-brown solid, m.p. 136-137° C.

$^1$H-NMR spectrum (300 MHz, internal standard: TMS, solvent CDCl$_3$) δ (ppm): 2.41 (s, 3H), 8.50 (s, 1H), 8.72 (s, 1H), 10.10 (s, 1H).

Example 5

The Preparation of Compound 285

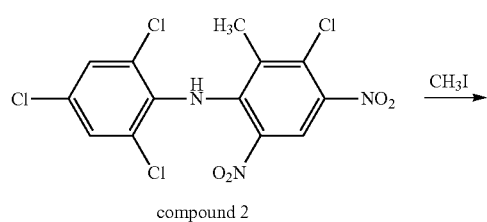

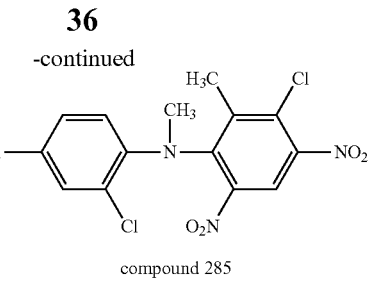

0.38 g (0.001 mol) of compound 2 was added to a suspension of 0.10 g (0.0025 mol) of NaH (60%) and 10 mL of DMF, the mixture was stirred for 1 h and then added thereto 0.43 g (0.003 mol) of CH$_3$I, the resulting mixture was allowed to react for 5 h. After the reaction was over by Thin-Layer Chromatography monitoring, the reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/10, as an eluent) to give 0.15 g of compound 285 as yellow solid, m.p. 142-144° C.

$^1$H-NMR spectrum (300 MHz, internal standard: TMS, solvent CDCl$_3$) δ (ppm): 2.54 (s, 3H), 3.31 (s, 3H), 7.09 (d, 1H), 7.25 (d, 2H), 8.04 (s, 1H).

Example 6

The Preparation of Compound 391

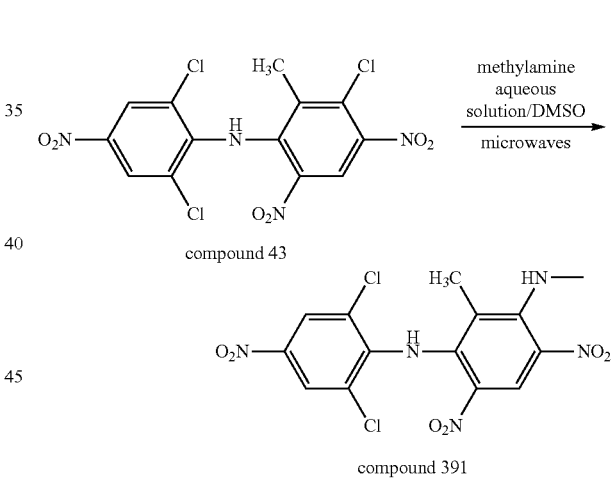

0.42 g of compound 43 (0.001 mol) was added to a microwave vial and dissolved with 2.5 mL of DMSO, 1 mL of methylamine aqueous solution (25%) was added, the vial was lidded and put into the microwave reactor, then the reaction was carried out at 150° C. for 40 min. The reaction mixture was poured into 50 mL of saturated brine and extracted with ethyl acetate, the extract was dried over anhydrous magnesium sulfate and concentrated under reduced pressure. The residue was purified through silica column (ethyl acetate/petroleum ether (boiling point range 60-90° C.)=1/20, as an eluent) to give 0.25 g of compound 391 as yellow solid, m.p. 218-219° C.

$^1$H-NMR spectrum (300 MHz, internal standard: TMS, solvent CDCl$_3$) δ (ppm): 1.70 (s, 3H), 3.09 (d, 3H), 8.25 (d, 1H), 8.31 (s, 2H), 9.12 (s, 1H), 9.58 (s, 1H).

Other compounds of the present invention were prepared according to the above examples.

Physical properties and ¹HNMR spectrum (¹HNMR, 300 MHz, internal standard: TMS, ppm) of some compounds of this invention are as follows:

Compound 1: m.p. 136-138° C. δ (CDCl₃): 2.12 (s, 3H), 7.21 (m, 2H), 7.26 (m, 1H), 8.72 (s, 1H), 9.00 (s, 1H).

Compound 4: m.p. 142-143° C. δ (CDCl₃): 2.20 (s, 3H), 6.59 (s, 1H), 7.58 (s, 1H), 8.67 (s, 1H), 8.80 (s, 1H).

Compound 5: m.p. 160-162° C. δ (CDCl₃): 1.95 (s, 3H), 7.41 (s, 2H), 8.72 (s, 1H), 9.19 (s, 1H).

Compound 7: m.p. 184-186° C. δ (CDCl₃): 2.22 (s, 3H), 6.87 (d, 2H), 7.62 (d, 2H), 8.66 (s, 1H), 8.93 (s, 1H).

Compound 8: m.p. 172-174° C. δ (DMSO): 2.34 (s, 3H), 6.83 (d, 2H), 8.06 (d, 2H), 8.64 (s, 1H), 9.49 (s, 1H).

Compound 9: m.p. 185-186° C. δ (CDCl₃): 2.41 (s, 3H), 6.56 (d, 1H), 8.31 (d, 1H), 8.52 (s, 1H), 9.23 (s, 1H), 10.59 (s, 1H).

Compound 10: a red oil. δ (CDCl₃): 2.27 (s, 3H), 8.52 (s, 1H), 9.09 (s, 2H), 10.93 (s, 1H).

Compound 12: m.p. 91-94° C. δ (CDCl₃): 2.14 (s, 3H), 6.91 (d, 2H), 7.21 (d, 2H), 8.71 (s, 1H), 9.20 (s, 1H).

Compound 28: m.p. 158-160° C. δ (CDCl₃): 2.10 (s, 3H), 6.83 (d, 4H), 7.12 (m, 2H), 7.34 (m, 4H), 8.56 (s, 1H).

Compound 31: m.p. 106-108° C. δ (CDCl₃): 2.22 (s, 3H), 6.55 (d, 1H), 7.43 (d, 1H), 7.75 (s, 1H), 8.65 (s, 1H), 8.87 (s, 1H).

Compound 32: m.p. 191-193° C. δ (CDCl₃): 2.29 (s, 3H), 6.48 (d, 1H), 8.06 (d, 1H), 8.41 (s, 1H), 8.62 (s, 1H), 8.79 (s, 1H).

Compound 33: m.p. 206-208° C. δ (CDCl₃): 2.25 (s, 3H), 6.48 (d, 1H), 7.47 (d, 1H), 7.77 (s, 1H), 8.62 (s, 1H), 8.80 (s, 1H).

Compound 34: m.p. 121-123° C. δ (CDCl₃): 2.02 (s, 3H), 2.40 (s, 3H), 6.53 (d, 1H), 7.10 (d, 1H), 7.27 (s, 1H), 8.74 (s, 1H), 9.03 (s, 1H).

Compound 36: m.p. 204-205° C. δ (CDCl₃): 2.31 (s, 3H), 6.48 (d, 1H), 7.43 (d, 1H), 8.26 (s, 1H), 8.54 (s, 1H), 10.36 (s, 1H).

Compound 39: m.p. 148-150° C. δ (CDCl₃): 2.07 (s, 3H), 7.53 (s, 1H), 7.72 (s, 1H), 8.71 (s, 1H), 8.97 (s, 1H).

Compound 41: m.p. 154-156° C. δ (CDCl₃): 2.21 (s, 3H), 7.20 (m, 1H), 7.80 (m, 1H), 8.59 (s, 1H), 9.94 (s, 1H).

Compound 42: m.p. 140-142° C. δ (CDCl₃): 2.17 (s, 3H), 7.19 (d, 2H), 8.71 (s, 1H), 8.94 (s, 1H).

Compound 44: m.p. 143-144° C. δ (CDCl₃): 1.98 (s, 3H), 7.66 (s, 2H), 8.70 (s, 1H), 9.10 (s, 1H).

Compound 45: m.p. 180-182° C. δ (CDCl₃): 1.99 (s, 3H), 7.69 (s, 2H), 8.67 (s, 1H), 9.00 (s, 1H).

Compound 47: m.p. 241-243° C. δ (CDCl₃): 1.97 (s, 3H), 7.83 (s, 2H), 8.69 (s, 1H), 9.11 (s, 1H).

Compound 51: m.p. 259-261° C. δ (CDCl₃): 2.38 (s, 3H), 6.54 (d, 1H), 7.70 (d, 1H), 8.50 (s, 1H), 8.62 (s, 1H), 10.51 (s, 1H).

Compound 61: m.p. 160-162° C. δ (CDCl₃): 2.18 (s, 3H), 7.88 (d, 1H), 8.32 (d, 1H), 8.55 (s, 1H), 9.97 (s, 1H).

Compound 62: m.p. 169-171° C. δ (CDCl₃): 2.26 (s, 3H), 8.50 (d, 2H), 8.99 (s, 1H), 10.14 (s, 1H).

Compound 63: m.p. 204-206° C. δ (CDCl₃): 2.23 (s, 3H), 7.87 (s, 1H), 8.38 (s, 1H), 8.51 (s, 1H), 10.00 (s, 1H).

Compound 67: m.p. 187-190° C. δ (CDCl₃): 2.18 (s, 3H), 8.23 (s, 2H), 8.57 (s, 1H), 10.39 (s, 1H).

Compound 69: m.p. 93-95° C. δ (CDCl₃): 2.19 (s, 3H), 8.14 (s, 2H), 8.56 (s, 1H), 10.42 (s, 1H).

Compound 77: an orange oil. δ (DMSO): 2.33 (s, 3H), 6.92 (d, 1H), 7.26 (s, 1H), 7.78 (s, 1H), 8.63 (s, 1H), 9.54 (s, 1H).

Compound 78: m.p. 204-206° C. δ (DMSO): 2.32 (s, 3H), 7.03 (s, 1H), 8.73 (s, 1H), 8.86 (s, 1H), 10.40 (s, 1H).

Compound 79: m.p. 125-127° C. δ (CDCl₃): 1.94 (s, 3H), 7.53 (s, 2H), 8.75 (s, 1H), 9.29 (s, 1H).

Compound 81: m.p. 160-161° C. δ (CDCl₃): 2.13 (s, 3H), 2.54 (s, 3H), 6.40 (d, 1H), 7.19 (d, 1H), 8.68 (s, 1H), 8.96 (s, 1H).

Compound 83: m.p. 110-112° C. δ (CDCl₃): 2.03 (s, 3H), 2.50 (s, 3H), 6.50 (d, 1H), 7.05 (t, 1H), 7.24 (d, 1H), 8.73 (s, 1H), 9.06 (s, 1H).

Compound 84: m.p. 133-135° C. δ (CDCl₃): 2.03 (s, 3H), 2.50 (s, 3H), 6.53 (d, 1H), 7.06 (t, 1H), 7.21 (d, 1H), 8.74 (s, 1H), 9.08 (s, 1H).

Compound 86: m.p. 158-161° C. δ (CDCl₃): 2.16 (s, 3H), 2.61 (s, 3H), 6.47 (d, 1H), 7.67 (d, 1H), 8.69 (s, 1H), 8.85 (s, 1H).

Compound 88: m.p. 172-175° C. δ (DMSO): 2.32 (s, 3H), 8.49 (s, 1H), 8.68 (s, 2H), 9.50 (s, 1H).

Compound 90: m.p. 127-129° C. δ (CDCl₃): 2.36 (s, 3H), 6.55 (s, 1H), 8.40 (s, 1H), 8.54 (s, 1H), 10.31 (s, 1H).

Compound 91: m.p. 169-171° C. δ (CDCl₃): 2.32 (s, 3H), 6.42 (s, 1H), 8.20 (s, 1H), 8.60 (s, 1H), 8.62 (s, 1H).

Compound 96: m.p. 159-162° C. δ (CDCl₃): 2.16 (s, 3H), 8.23 (s, 1H), 8.63 (s, 1H), 8.91 (s, 1H).

Compound 97: m.p. 133-135° C. δ (CDCl₃): 2.07 (s, 3H), 7.70 (s, 1H), 8.69 (s, 1H), 9.22 (s, 1H).

Compound 101: m.p. 96-97° C. δ (CDCl₃): 2.21 (s, 3H), 5.08 (m, 1H), 6.59 (s, 1H), 7.49 (s, 1H), 8.66 (s, 1H), 8.78 (s, 1H).

Compound 102: m.p. 192-194° C. δ (CDCl₃): 2.20 (s, 3H), 7.05 (s, 2H), 8.04 (s, 1H), 8.22 (s, 1H), 9.07 (s, 1H), 9.43 (s, 1H).

Compound 106: m.p. 112-114° C. δ (CDCl₃): 2.18 (s, 3H), 6.38 (s, 1H), 7.38 (d, 1H), 7.50 (s, 1H), 7.97 (d, 1H), 8.11 (s, 1H).

Compound 109: m.p. 146-148° C. δ (CDCl₃): 2.19 (s, 3H), 6.70 (d, 2H), 7.36 (d, 1H), 7.53 (d, 1H), 7.96 (d, 1H), 8.20 (s, 1H).

Compound 110: m.p. 136-138° C. δ (CDCl₃): 2.22 (s, 3H), 6.70 (d, 2H), 7.41 (d, 1H), 8.00 (d, 1H), 8.16 (d, 2H), 8.22 (s, 1H).

Compound 113: m.p. 72-74° C. δ (CDCl₃): 2.12 (s, 3H), 6.75 (d, 2H), 7.12 (d, 2H), 7.25 (d, 1H), 7.98 (d, 1H), 8.46 (s, 1H).

Compound 116: a red oil. δ (CDCl₃): 2.02 (s, 3H), 2.38 (s, 3H), 6.34 (d, 1H), 7.00 (d, 1H), 7.18 (m, 2H), 7.98 (d, 1H), 8.30 (s, 1H).

Compound 120: a brown oil. δ (CDCl₃): 1.92 (s, 3H), 7.22 (d, 1H), 7.58 (s, 2H), 7.93 (d, 1H), 8.39 (s, 1H).

Compound 126: m.p. 158-160° C. δ (CDCl₃): 2.30 (s, 3H), 6.47 (d, 1H), 7.59 (m, 2H), 7.94 (d, 1H), 8.60 (s, 1H), 10.21 (s, 1H).

Compound 136: m.p. 136-138° C. δ (CDCl₃): 2.22 (s, 3H), 6.75 (d, 1H), 7.03 (s, 1H), 7.45 (d, 1H), 7.67 (d, 1H), 7.99 (d, 1H), 8.16 (s, 1H).

Compound 347: m.p. 134-136° C. δ (CDCl₃): 1.79 (s, 3H), 3.96 (s, 3H), 8.29 (s, 2H), 8.74 (s, 1H), 9.18 (s, 1H).

Compound 369: m.p. 132-134° C. δ (CDCl₃): 2.11 (s, 3H), 2.39 (s, 3H), 8.29 (s, 2H), 8.47 (s, 1H), 8.95 (s, 1H).

Compound 413: m.p. 178-180° C. δ (CDCl₃): 1.71 (s, 3H), 2.86 (s, 6H), 8.29 (s, 2H), 8.66 (s, 1H), 9.45 (s, 1H).

Compound 457: m.p. 126-128° C. δ (CDCl₃): 1.83 (s, 3H), 4.42 (q, 2H), 8.30 (s, 2H), 8.85 (s, 1H), 9.20 (s, 1H).

Compound 501: m.p. 151-153° C. δ (CDCl₃): 1.99 (s, 3H), 8.31 (d, 1H), 8.47 (d, 1H), 8.66 (s, 1H), 9.00 (s, 1H).

Compound 502: m.p. 151-154° C. δ (CDCl₃): 1.97 (s, 3H), 8.49 (s, 1H), 8.68 (s, 1H), 9.03 (s, 1H).

Compound 503: m.p. 132-134° C. δ (CDCl₃): 1.95 (s, 3H), 3.96 (s, 3H), 8.05 (s, 2H), 8.70 (s, 1H), 9.13 (s, 1H).

Compound 504: m.p. 135-137° C. δ (CDCl₃): 2.16 (s, 3H), 7.95 (dd, 1H), 8.26 (t, 1H), 8.63 (s, 1H), 8.82 (s, 1H).

Compound 505: m.p. 131-132° C. δ (CDCl₃): 2.10 (s, 3H), 6.99 (t, 2H), 7.17 (m, 1H), 8.72 (s, 1H), 8.98 (s, 1H).

Compound 506: m.p. 148-150° C. δ (CDCl₃): 2.12 (s, 3H), 7.04 (d, 2H), 8.70 (s, 1H), 8.87 (s, 1H).

Compound 507: m.p. 140-142° C. δ (CDCl₃): 2.58 (s, 3H), 3.30 (s, 3H), 8.38 (s, 1H), 8.57 (s, 2H).

Compound 508: δ(CDCl₃): 1.94 (s, 3H), 3.03 (d, 3H), 7.78 (s, 2H), 8.70 (s, 1H), 9.14 (s, 1H).

Compound 509: m.p. 216-218° C. δ (CDCl₃): 1.56 (s, 3H), 3.04 (m, 6H), 7.80 (s, 2H), 8.18 (s, 1H), 9.13 (s, 1H), 9.58 (s, 1H).

Compound 510: m.p. 138-140° C. δ (CDCl₃): 2.58 (s, 3H), 3.37 (s, 3H), 7.23 (d, 1H), 7.48 (s, 1H), 7.57 (d, 1H), 8.08 (s, 1H).

Compound 511: m.p. 216-219° C. δ (CDCl₃): 2.30 (s, 3H), 7.88 (s, 2H), 8.48 (s, 1H), 8.85 (s, 1H).

Compound 521: m.p. 146-148° C. δ (CDCl₃): 1.86 (s, 3H), 2.40 (s, 3H), 7.18 (m, 2H), 7.28 (m, 1H), 8.80 (s, 1H), 9.52 (s, 1H).

Compound 522: m.p. 137-139° C. δ (CDCl₃): 1.91 (s, 3H), 2.31 (s, 3H), 8.10 (s, 1H), 8.21 (s, 1H), 8.73 (s, 1H), 9.20 (s, 1H).

FORMULATION EXAMPLES

The active ingredient can be selected from any compound of general formula I of the present invention, base on 100% active ingredient (Weight/Weight %).

Example 7

30% Wettable Powders

| | |
|---|---|
| Compound 43 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

The compound and other components are fully mixed, after smashing through ultrafine pulverizer, 30% wettable powder products were obtained.

Example 8

40% Suspension Concentrate

| | |
|---|---|
| Compound 38 | 40% |
| Glycol | 10% |
| Nonylphenols polyethylene glycol ether | 6% |
| Lignin sulfonate | 10% |
| Carboxymethyl cellulose | 1% |
| 37% of formaldehyde aqueous solution | 0.2% |
| 75% of silicone oil water emulsion | 0.8% |
| Water | Make up to 100% |

Fully mixing the compound and other components, suspension concentrate can be obtained, and then any required dilution can be obtained by diluting the above suspension concentrate with water.

Example 9

60% Water Dispersible Granules

| | |
|---|---|
| Compound 38 | 60% |
| Naphthalene sulfonate formaldehyde condensate | 12% |
| N-methyl-N-oil acyl - bovine sodium | 8% |
| Polyvinylpyrrolidone | 2% |
| Carboxymethyl cellulose | 2% |
| Kaolin | Make up to 100% |

The compound and other components were mixed and smashed, then kneaded together with water, added to the granulation 10-100 mesh machine for granulation, finally dried and sieved (at the scope screen).

Biological Testing

The compounds of the present invention showed excellent activity against a variety of plant pathogens/diseases in agricultural field, but didn't exhibit any herbicidal activity so far. The tests of compounds of the present invention against many kinds of plant diseases caused by fungi were carried out in vitro or in vivo. The results of fungicidal activity are listed in the following examples.

Example 10

Determination of the Activity In Vitro

The method is as follow:

High Through Put is used in the test. The compound is dissolved in a proper solvent to become a testing solution whose concentration is designed. The solvent is selected from acetone, methanol, DMF and so on according to their dissolving capability to the sample. In a no animalcule condition, the testing solution and pathogens suspension are added into the cells of 96 cells culture board, which then should be placed in the constant temperature box. 24 hours later, pathogen germination or growth can be investigated by eyeballing, and the activity in vitro of the compound is evaluated based on germination or growth of control treatment.

The activities in vitro (inhibition rate) of parts of the compounds are as follows:

The inhibition rate against rice blast (*Magnaporthe grisea*):

At the dose of 25 mg/L, the inhibition rate of compounds 2, 4, 5, 7, 8, 9, 10, 12, 28, 32, 36, 38, 39, 41, 42, 43, 44, 45, 47, 51, 62, 63, 67, 69, 77, 78, 79, 83, 84, 86, 88, 89, 90, 91, 96, 97, 102, 109, 110, 116, 126, 136, 347, 369, 413, 457, 501, 502, 503, 504, 506, 507 and so on was 100%;

At the dose of 2.8 mg/L, the inhibition rate of compounds 5, 9, 12, 32, 38, 39, 41, 42, 43, 44, 45, 51, 62, 63, 67, 69, 77, 78, 86, 89, 90, 91, 96, 97, 126, 347, 369, 413, 457, 501, 502, 503, 504, 506 was 100%, and that of compounds 2, 4, 8, 36, 79, 88 was 80%;

At the dose of 0.3 mg/L, the inhibition rate of compounds 38, 39, 42, 43, 44, 45, 67, 91, 97, 347, 369, 457, 501, 502, 504 was 100%, and that of compound 413 was 80%;

At the dose of 0.03 mg/L, the inhibition rate of compounds 42, 369, 504 was 100%, and that of compounds 43, 45, 347, 501 was 80%.

The inhibition rate against cucumber gray mold (*Botrytis cinerea*):

At the dose of 25 mg/L, the inhibition rate of compounds 38, 39, 42, 43, 44, 45, 62, 63, 67, 69, 78, 88, 89, 90, 91, 96, 97, 457 was 100%;

At the dose of 2.8 mg/L, the inhibition rate of compounds 38, 39, 42, 43, 44, 45, 62, 63, 67, 69, 78, 89, 91, 97, 457 was 100%, and that of compounds 88, 96 was 80%;

At the dose of 0.3 mg/L, the inhibition rate of compounds 42, 43, 45, 457 was 100%, and that of compounds 38, 39, 67, 97 was 80%;

At the dose of 0.03 mg/L, the inhibition rate of compound 42 was 100%.

Example 11

The Determination of Protectant Activity In Vivo

The method is as follow:

The whole plant is used in this test. The compound is dissolved in a proper solvent to get mother solution. The proper solvent is selected from acetone, methanol, DMF and so on according to their dissolving capability to the sample. The rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protectant activities in vivo of parts of the compounds are as follows:

The protectant activity against cucumber downy mildew (*Pseudoperonospora cubensis*) in vivo:

At the dose of 400 mg/L, the protectant activity of compounds 5, 9, 10, 32, 38, 39, 43, 44, 45, 62, 63, 67, 69, 77, 78, 88, 89, 91, 96, 413, 501, 522 was 100%, and that of compounds 41, 86, 391, 502, 503, 504, 507 was more than 90%;

At the dose of 100 mg/L, the protectant activity of compounds 5, 9, 10, 32, 38, 39, 43, 44, 45, 62, 63, 67, 69, 78, 88, 89 was 100%, that of compounds 77, 91, 96 was more than 95% and that of compounds 41, 86, 504 was no less than 85%;

At the dose of 50 mg/L, the protectant activity of compounds 9, 38, 39, 43, 44, 63, 67, 69, 78, 88 was 100%, that of compound 62 was 98% and that of compounds 32, 45, 91 was no less than 70%;

At the dose of 12.5 mg/L, the protectant activity of compounds 43, 63, 78 was 100%, and that of compounds 38, 44, 67, 91 was no less than 80%.

The protectant activity against corn rust (*Puccinia sorghi*) in vivo:

At the dose of 400 mg/L, the protectant activity of compounds 2, 12, 32, 34, 38, 41, 42, 43, 44, 63, 67, 78, 84, 89, 102, 347, 502 was 100%, that of compounds 36, 88, 136, 369, 413, 501, 503, 504, 505 was no less than 95% and that of compounds 4, 39, 69, 81, 110, 116, 120, 391 was no less than 80%;

At the dose of 100 mg/L, the protectant activity of compounds 43, 44, 78, 347, 369, 502 was 100%, and that of compounds 34, 67, 84, 88, 413, 501 was no less than 80%;

At the dose of 25 mg/L, the protectant activity of compounds 347, 369 was 100%, and that of compounds 34, 44, 88, 502 was no less than 60%;

At the dose of 6.25 mg/L, the protectant activity of compound 347 was 100%, and that of compound 369 was 85%.

The protectant activity against wheat powdery mildew (*Blumeria graminis*) in vivo:

At the dose of 400 mg/L, the protectant activity of compound 63 was 100%, and that of compounds 43, 45, 67, 90 was no less than 80%.

The protectant activity against cucumber anthracnose (*Colletotrichum lagenarium*) in vivo:

At the dose of 400 mg/L, the protectant activity of compounds 43, 44, 78 was 100%.

Example 12

The Test Results of Parts of Compounds and Contrasts

Contrastive tests were carried out between parts of compounds, contrasts and intermediates. The test results are listed in table 7-table 11 ("/" in the following tables means no test).

TABLE 7

| | The protectant activity against cucumber downy mildew in vivo | | |
|---|---|---|---|
| | Protectant activity (%) | | |
| Compd. No. | 50 mg/L | 12.5 mg/L | 3.125 mg/L |
| 38 | 100 | 80 | 65 |
| 43 | 100 | 100 | 90 |
| 44 | 100 | 85 | 45 |
| 45 | 80 | 65 | 55 |
| 67 | 100 | 80 | 40 |
| 69 | 100 | 70 | 40 |
| 78 | 100 | 100 | 60 |
| 91 | 95 | 80 | 75 |
| intermediate B | 0 | 0 | 0 |
| intermediate C | 0 | 0 | 0 |
| diphenylamine | 0 | 0 | 0 |
| fluazinam | 100 | 95 | 40 |
| dimethomorph | 100 | 80 | 35 |
| contrast ACS | 0 | 0 | 0 |

Contrast ACS was reported in ACS Symposium Series (1992), 504 (Synth. Chem. Agrochem. III), 341-48, its structure is as follow:

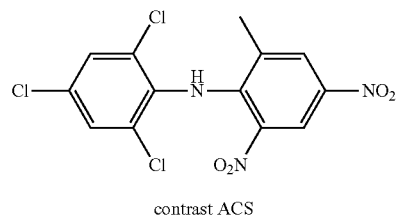 [SMILES: Cc1cc([N+](=O)[O-])cc([N+](=O)[O-])c1Nc1c(Cl)cc(Cl)cc1Cl]

contrast ACS

TABLE 8

The protectant activity against corn rust in vivo:

| Compd. No. | Protectant activity (%) | | |
|---|---|---|---|
| | 100 mg/L | 25 mg/L | 6.25 mg/L |
| 34 | 80 | 75 | 20 |
| 38 | 70 | 20 | 0 |
| 44 | 75 | 60 | 15 |
| 84 | 90 | 30 | 0 |
| 88 | 90 | 60 | 0 |
| 347 | 100 | 100 | 100 |
| 369 | 100 | 100 | 85 |
| 413 | 85 | 30 | 0 |
| 501 | 85 | 50 | 30 |
| 502 | 100 | 60 | 20 |
| fluazinam | 90 | 30 | 10 |
| contrast ACS | 0 | 0 | 0 |

TABLE 9

The activity against rice blast and cucumber gray mold in vitro

| Compd. No. | Inhibition rate against rice blast (%) | | Inhibition rate against cucumber gray mold (%) | | |
|---|---|---|---|---|---|
| | 0.3 mg/L | 0.03 mg/L | 0.3 mg/L | 0.1 mg/L | 0.03 mg/L |
| 38 | / | / | 80 | 50 | 0 |
| 39 | / | / | 80 | 50 | 0 |
| 42 | 100 | 100 | 100 | 100 | 100 |
| 43 | 100 | 80 | 100 | 100 | 50 |
| 45 | 100 | 80 | 100 | 100 | 0 |
| 347 | 100 | 80 | / | / | / |
| 369 | 100 | 100 | / | / | / |
| 457 | 100 | 50 | 100 | 80 | 0 |
| 501 | 100 | 80 | / | / | / |
| 502 | 100 | 50 | / | / | / |
| 504 | 100 | 100 | / | / | / |
| fluazinam | 100 | 50 | 100 | 80 | 0 |
| contrast ACS | 0 | 0 | 0 | 0 | 0 |

TABLE 10

Contrastive results of compound 43 and contrast ACS

| Compd. No. | Protectant activity against cucumber downy mildew in vivo (%) | | | Activity against rice blast in vitro (%) | | | |
|---|---|---|---|---|---|---|---|
| | 100 mg/L | 50 mg/L | 25 mg/L | 25 mg/L | 8.3 mg/L | 2.8 mg/L | 0.9 mg/L |
| 5 | 100 | 40 | 30 | 100 | 100 | 100 | 100 |
| contrast ACS | / | 0 | 0 | 0 | 0 | 0 | 0 |

TABLE 11

Contrastive results of compound 43 and fluazinam

| Target fungus | Compound | Activity in vitro (%) | | |
|---|---|---|---|---|
| | | 10 mg/L | 1 mg/L | 0.1 mg/L |
| rice sheath blight | compound 43 | 100 | 95 | 74 |
| (*Rhizoctonia solani* Palo) | fluazinam | 97 | 83 | 69 |
| corn southern leaf blight | compound 43 | 100 | 100 | 54 |
| (*Helminthosporium maydis*) | fluazinam | 100 | 92 | 41 |
| cucumber fusarium wilt | compound 43 | 99 | 91 | 79 |
| (*Fusarium oxysporum* f. sp.) | fluazinam | 92 | 85 | 56 |
| pear scab (*Fusicladium pirina*) | compound 43 | 100 | 99 | 87 |
| | fluazinam | 94 | 89 | 47 |
| cotton nthracnose (*Colletotrichum gossypii* Southw.) | compound 43 | 100 | 100 | 94 |
| | fluazinam | 100 | 97 | 71 |
| cotton verticillium wilt (*Verticillium dahliae* Kleb) | compound 43 | 100 | 100 | 82 |
| | fluazinam | 100 | 96 | 46 |
| rape sclertiniose (*Sclerotinia sclerotiorum*) | compound 43 | 100 | 100 | 88 |
| | fluazinam | 100 | 97 | 57 |

We claim:

1. A substituted diphenylamine compound having general formula I:

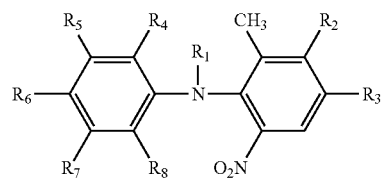

wherein:

$R_1$ is selected from H, $C_1$-$C_{12}$alkyl, $C_3$-$C_{12}$cycloalkyl, $C_1$-$C_{12}$haloalkyl, $C_1$-$C_{12}$alkylcarbonyl, $C_1$-$C_{12}$haloalkylcarbonyl, $C_1$-$C_{12}$alkoxycarbonyl, $C_1$-$C_{12}$alkylaminocarbonyl, $C_1$-$C_{12}$alkylthio, $C_1$-$C_{12}$haloalkylthio, $C_1$-$C_{12}$alkylsulfonyl, $C_1$-$C_{12}$alkoxy$C_1$-$C_{12}$alkyl, $C_1$-$C_{12}$alkoxy$C_1$-$C_{12}$alkylcarbonyl, $C_1$-$C_{12}$alkoxycarbonyl$C_1$-$C_{12}$alkyl, $C_1$-$C_{12}$alkylaminothio, $C_2$-$C_{12}$ dialkylaminothio or CO—X—$CO_2R_9$, in which X is selected from $(CHR_9)n$, $CR_9$=$CR_{10}$ or $C_6H_4$, n=1-6;

$R_2$ is selected from halogen, $C_1$-$C_{12}$haloalkyl, $C_1$-$C_{12}$alkoxy, $C_1$-$C_{12}$haloalkoxy, $C_1$-$C_{12}$alkylamino, $C_1$-$C_{12}$haloalkylamino, $C_1$-$C_{12}$alkylthio, $C_1$-$C_{12}$haloalkylthio, $C_1$-$C_{12}$alkylsulfonyl, $C_3$-$C_{12}$cycloalkyl, $C_2$-$C_{12}$dialkylamino, $C_3$-$C_{12}$alkenyloxy, $C_3$-$C_{12}$haloalkenyloxy, $C_3$-$C_{12}$alkynyloxy, $C_3$-$C_{12}$haloalkynyloxy, $C_1$-$C_{12}$alkylcarbonyloxy, $C_1$-$C_{12}$alkylcarbonylamino, $C_1$-$C_{12}$alkylsulfonyloxy, $C_1$-$C_{12}$alkoxy$C_1$-$C_{12}$alkoxy, $C_1$-$C_{12}$alkoxycarbonyl$C_1$-$C_{12}$alkoxy, or the following groups unsubstituted or substituted with 1-5 $R_{11}$: aryloxy, arylamino, arylmethoxy, arylmethylamino, heteroaryloxy or heteroarylamino, and when the number of the substitutes is more than 1, $R_{11}$ may be the same or different;

$R_3$ is selected from H, halogen, $NO_2$, CN, C(=O)$NR_9R_{10}$, C(=S)$NR_9R_{10}$, $C_1$-$C_{12}$alkylaminocarbonyl, $C_1$-$C_{12}$alkoxycarbonyl, $C_1$-$C_{12}$haloalkyl or $C_1$-$C_{12}$alkylsulfonyl;

$R_4$ and $R_8$ may be the same or different, respectively selected from H, halogen, CN, $NO_2$, C(=O)$NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

$R_5$ and $R_7$ may be the same or different, respectively selected from H, halogen, CN, $NO_2$, $C(=O)NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylamino, $C_1$-$C_{12}$haloalkylamino, $C_1$-$C_{12}$alkylthio, $C_1$-$C_{12}$haloalkylthio, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkylcarbonyloxy, $C_1$-$C_{12}$alkoxycarbonyloxy, $C_1$-$C_{12}$alkylaminocarbonyloxy, $C_1$-$C_{12}$alkylsulfonyloxy, $C_1$-$C_{12}$alkoxy$C_1$-$C_{12}$alkoxy, $C_1$-$C_{12}$haloalkoxy$C_1$-$C_{12}$haloalkoxy, $C_1$-$C_{12}$alkoxycarbonyl$C_1$-$C_{12}$alkoxy, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

$R_6$ is selected from H, halogen, CN, $NO_2$, $CO_2H$, $C(=O)NR_9R_{10}$, $C_1$-$C_{12}$alkyl, $C_1$-$C_{12}$haloalkyl, $C_1$-$C_{12}$alkoxy, $C_1$-$C_{12}$haloalkoxy, $C_2$-$C_{12}$alkenyl, $C_2$-$C_{12}$alkynyl, $C_1$-$C_{12}$alkylsulfonyl, $C_1$-$C_{12}$alkylcarbonyl, $C_1$-$C_{12}$alkoxycarbonyl, $C_1$-$C_{12}$alkoxy$C_1$-$C_{12}$alkyl, $C_1$-$C_{12}$alkoxycarbonyl$C_1$-$C_{12}$alkyl, $C_1$-$C_{12}$alkoxy$C_1$-$C_{12}$alkoxy, $C_1$-$C_{12}$haloalkoxy$C_1$-$C_{12}$haloalkoxy, or the following groups unsubstituted or substituted with 1-5 $R_{11}$: aryl, arylmethyl, aryloxy, arylamino, arylcarbonyl, arylmethylcarbonyl, aryloxycarbonyl, arylaminocarbonyl or heteroaryloxy, and when the number of the substitutes is more than 1, $R_{11}$ may be the same or different;

but $R_4$, $R_5$, $R_6$, $R_7$ and $R_8$ can not be H simultaneously;

$R_9$ and $R_{10}$ may be the same or different, respectively selected from H or $C_1$-$C_6$alkyl;

$R_{11}$ is selected from halogen, $NO_2$, ON, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylcarbonyl, $C_1$-$C_6$alkoxycarbonyl, $C_2$-$C_6$alkenyl, $C_2$-$C_6$haloalkenyl, $C_3$-$C_6$alkenyloxy, $C_3$-$C_6$haloalkenyloxy, $C_2$-$C_6$alkynyl, $C_2$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$haloalkylamino, $C_2$-$C_8$dialkylamino, $C_1$-$C_6$alkylcarbonylamino, $C_1$-$C_6$haloalkylcarbonylamino, $C_1$-$C_6$alkylaminocarbonyl or $C_1$-$C_6$haloalkylaminocarbonyl;

or the salts of the compounds having general formula I.

2. The compound according to the claim 1, characterized in that wherein general formula I:

$R_1$ is selected from H, $C_1$-$C_6$alkyl, $C_3$-$C_6$cycloalkyl, $C_1$-$C_6$alkylcarbonyl, $C_1$-$C_6$haloalkylcarbonyl, $C_1$-$C_6$alkoxycarbonyl, $C_1$-$C_6$alkylthio, $C_1$-$C_6$haloalkylthio, $C_1$-$C_6$alkylsulfonyl, $C_1$-$C_6$alkoxy$C_1$-$C_6$alkyl, $C_1$-$C_6$alkoxy$C_1$-$C_6$alkylcarbonyl, $C_1$-$C_6$alkoxycarbonyl$C_1$-$C_6$alkyl, $C_1$-$C_6$alkylaminothio, $C_2$-$C_6$ dialkylaminothio or CO—X—$CO_2R_9$, in which X is selected from $(CHR_9)n$, $CR_9=CR_{10}$ or $C_6H_4$, n=1-3;

$R_2$ is selected from halogen, $C_1$-$C_6$alkoxy, $C_1$-$C_6$haloalkoxy, $C_1$-$C_6$alkylamino, $C_1$-$C_6$haloalkylamino, $C_1$-$C_6$alkylthio, $C_1$-$C_6$haloalkylthio, $C_1$-$C_6$alkylsulfonyl, $C_2$-$C_6$dialkylamino, $C_3$-$C_6$alkenyloxy, $C_3$-$C_6$haloalkenyloxy, $C_3$-$C_6$alkynyloxy, $C_1$-$C_6$alkylcarbonyloxy, $C_1$-$C_6$alkylcarbonyloxy, $C_1$-$C_6$alkylsulfonyloxy, $C_1$-$C_6$alkoxy$C_1$-$C_6$alkoxy, $C_1$-$C_6$alkoxycarbonyl$C_1$-$C_6$alkoxy, or the following groups unsubstituted or substituted with 1-3 $R_{11}$: phenoxy, anilino, benzyloxy, benzylamino, pyridyloxy or pyridylamino;

$R_3$ is selected from Cl, Br, F, $NO_2$, CN, $C(=O)NR_9R_{10}$, $C(=S)NR_9R_{10}$, $CO_2CH_3$, $CF_3$ or $SO_2CH_3$;

$R_4$ and $R_8$ may be the same or different, respectively selected from H, halogen, CN, $NO_2$, $C(=O)NR_9R_{10}$, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, or the following groups unsubstituted or substituted with 1-4 $R_{11}$: phenoxy, anilino, phenylcarbonyl, benzylcarbonyl, phenoxycarbonyl, anilinocarbonyl or pyridyloxy;

$R_5$ and $R_7$ may be the same or different, respectively selected from H, halogen, CN, $NO_2$, $C(=O)NR_9R_{10}$, $C_1$-$C_6$alkyl, $C_1$-$C_6$haloalkyl, $C_1$-$C_6$alkoxy, $C_1$-$C_6$haloalkoxy, $C_1$-$C_6$alkylamino, $C_1$-$C_6$haloalkylamino, $C_1$-$C_6$alkylthio, $C_1$-$C_6$haloalkylthio, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl, $C_1$-$C_6$alkoxy$C_1$-$C_6$alkyl;

$R_6$ is selected from H, halogen, CN, $NO_2$, $CO_2H$, $C(=O)NR_9R_{10}$, $C_1$-$C_6$alkyl, $C_1$-$C_6$haloalkyl, $C_1$-$C_6$haloalkoxy, $C_2$-$C_6$alkenyl, $C_2$-$C_6$alkynyl, $C_1$-$C_6$alkylsulfonyl, $C_1$-$C_6$alkylcarbonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, $C_1$-$C_6$alkoxy$C_1$-$C_6$alkoxy, or the following groups unsubstituted or substituted with 1-4 $R_{11}$: phenoxy, anilino, phenylcarbonyl, benzylcarbonyl, phenoxycarbonyl, anilinocarbonyl or pyridyloxy;

but $R_4$, $R_5$, $R_6$, $R_7$ and $R_8$ can not be H simultaneously;

$R_9$ and $R_{10}$ may be the same or different, respectively selected from H or $C_1$-$C_3$alkyl;

$R_{11}$ is selected from halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylcarbonyl, $C_1$-$C_3$alkoxycarbonyl, $C_1$-$C_3$alkylamino, $C_2$-$C_6$dialkylamino, $C_1$-$C_3$alkylcarbonylamino or $C_1$-$C_3$alkylaminocarbonyl;

or the salts of the compounds having general formula I.

3. The compound according to the claim 2, characterized in that wherein general formula I:

$R_1$ is selected from H, $C_1$-$C_3$alkyl, $C_3$-$C_6$cycloalkyl, $C_1$-$C_3$alkylcarbonyl, $C_1$-$C_3$haloalkylcarbonyl, $C_1$-$C_3$alkoxycarbonyl, $C_1$-$C_3$haloalkylthio, $C_1$-$C_3$alkylsulfonyl, $C_1$-$C_3$alkoxy$C_1$-$C_3$alkyl, $C_1$-$C_3$alkoxy$C_1$-$C_3$alkylcarbonyl, $C_1$-$C_3$alkoxycarbonyl$C_1$-$C_3$alkyl, $C_1$-$C_3$alkylaminothio, $C_2$-$C_6$ dialkylaminothio or CO—X—$CO_2R_9$, in which X is selected from $(CHR_9)n$, $CR_9=CR_{10}$ or $C_6H_4$, n=1-3;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_2$-$C_6$dialkylamino, $C_3$-$C_4$alkenyloxy, $C_3$-$C_4$haloalkenyloxy, $C_3$-$C_4$alkynyloxy, $C_1$-$C_3$alkylcarbonyloxy, $C_1$-$C_3$alkylcarbonylamino, $C_1$-$C_3$alkylsulfonyloxy, $C_1$-$C_3$alkoxy$C_1$-$C_3$alkoxy, $C_1$-$C_3$alkoxycarbonyl$C_1$-$C_3$alkoxy, or the following groups unsubstituted or substituted with 1-3 $R_{11}$: phenoxy, anilino, benzyloxy, benzylamino, pyridyloxy or pyridylamino;

$R_3$ is $NO_2$, $R_4$ and $R_8$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_3$alkyl, $C_1$-$C_3$alkoxycarbonyl$C_1$-$C_3$alkyl, or the following groups unsubstituted or substituted with 1-3 $R_{11}$: phenoxy, anilino, phenylcarbonyl, benzylcarbonyl, phenoxycarbonyl, anilinocarbonyl or pyridyloxy;

$R_5$ and $R_7$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl or $C_1$-$C_3$alkoxy$C_1$-$C_3$alkyl;

$R_6$ is selected from H, Cl, Br, F, CN, $NO_2$, $CO_2H$, $C(=O)NR_9R_{10}$, $C_1$-$C_3$alkyl, $C_1$-$C_3$haloalkyl, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_6$alkyl, $C_1$-$C_3$alkoxycarbonyl$C_1$-$C_3$alkyl, $C_1$-$C_3$alkoxy$C_1$-$C_3$alkoxy, or the following groups unsubstituted or substituted with 1-3 $R_{11}$: phenoxy, anilino, phenylcarbonyl, benzylcarbonyl, phenoxycarbonyl, anilinocarbonyl or pyridyloxy;

but $R_4$, $R_5$, $R_6$, $R_7$ and $R_8$ can not be H simultaneously;

$R_9$ and $R_{10}$ may be the same or different, respectively selected from H or $C_1$-$C_3$alkyl;

$R_{11}$ is selected from Cl, Br, F, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylcarbonyl, $C_1$-$C_3$alkoxycarbonyl, or $C_1$-$C_3$alkylaminocarbonyl;

or the salts formed from the compounds of general formula I with hydrochloric acid, sulfuric acid, phosphoric acid, formic acid, acetic acid, trifluoroacetic acid, methylsulfonic acid, p-toluenesulfonic acid, malic acid or citric acid.

4. The compound according to the claim 3, characterized in that wherein general formula I:

$R_1$ is selected from H, $C_1$-$C_3$alkyl, $C_3$-$C_6$cycloalkyl, $C_1$-$C_3$alkylcarbonyl, $C_1$-$C_3$haloalkylcarbonyl, $C_1$-$C_3$alkoxycarbonyl, $C_1$-$C_3$haloalkylthio, $C_1$-$C_3$alkylsulfonyl, $C_1$-$C_3$alkoxy$C_1$-$C_3$alkyl, $C_1$-$C_3$alkoxy$C_1$-$C_3$alkylcarbonyl, $C_1$-$C_3$alkoxycarbonyl$C_1$-$C_3$alkyl, $C_1$-$C_3$alkylaminothio, $C_2$-$C_6$ dialkylaminothio, $COCH_2CO_2R_9$, $COCH_2CH_2CO_2R_9$, $COCHCH_3CO_2R_9$, $COC_6H_4CO_2R_9$ or $COCH=CHCO_2R_9$;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_2$-$C_6$dialkylamino, $C_3$-$C_4$alkenyloxy, $C_3$-$C_4$alkynyloxy, $C_1$-$C_3$alkoxy$C_1$-$C_3$alkoxy, $C_1$-$C_3$alkoxycarbonyl$C_1$-$C_3$alkoxy, or the following groups unsubstituted or substituted with 1-3 $R_{11}$: phenoxy, anilino, benzyloxy, benzylamino, pyridyloxy or pyridylamino;

$R_3$ is $NO_2$, $R_4$ and $R_8$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_3$alkyl, $C_1$-$C_3$alkoxycarbonyl$C_1$-$C_3$alkyl, or the following groups unsubstituted or substituted with 1-3 $R_{11}$: phenoxy, anilino, phenoxycarbonyl or anilinocarbonyl;

$R_5$ and $R_7$ may be the same or different, respectively selected from H, Cl, Br, F, CN, $NO_2$, $C(=O)NR_9R_{10}$, $C_1$-$C_3$alkyl, $C_1$-$C_3$haloalkyl, $C_1$-$C_3$alkoxy, $C_1$-$C_3$haloalkoxy, $C_1$-$C_3$alkylamino, $C_1$-$C_3$haloalkylamino, $C_1$-$C_3$alkylthio, $C_1$-$C_3$haloalkylthio, $C_1$-$C_3$alkylsulfonyl, $C_1$-$C_3$alkylcarbonyl, $C_1$-$C_3$alkoxycarbonyl or $C_1$-$C_3$alkoxy$C_1$-$C_3$alkyl;

$R_6$ is selected from H, Cl, Br, F, CN, $NO_2$, $CO_2H$, $C(=O)NR_9R_{10}$, $C_1$-$C_3$alkyl, $C_1$-$C_3$haloalkyl, $C_1$-$C_3$haloalkoxy, $C_2$-$C_3$alkenyl, $C_2$-$C_3$alkynyl, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_6$alkyl, $C_1$-$C_3$alkoxycarbonyl$C_1$-$C_3$alkyl, $C_1$-$C_3$alkoxy$C_1$-$C_3$alkoxy, or the following groups unsubstituted or substituted with 1-3 $R_{11}$: phenoxy, phenylcarbonyl, benzylcarbonyl, phenoxycarbonyl or anilinocarbonyl;

but $R_4$, $R_5$, $R_6$, $R_7$ and $R_8$ can not be H simultaneously;

$R_9$ and $R_{10}$ may be the same or different, respectively selected from H, $CH_3$ or $C_2H_5$;

$R_{11}$ is selected from Cl, Br, F, $NO_2$, CN, $CF_3$, $CH_3$, $OCH_3$, $SCH_3$, formyl, $CO_2CH_3$ or $CONHCH_3$;

or the salts formed from the compounds of general formula I with hydrochloric acid, sulfuric acid, phosphoric acid, formic acid, acetic acid, trifluoroacetic acid, methylsulfonic acid, p-toluenesulfonic acid, malic acid or citric acid.

5. The compound according to the claim 4, characterized in that wherein general formula I:

$R_1$ is selected from H, $CH_3$, $C_2H_5$, cyclopropyl, formyl, $COCH_3$, $COCF_3$, $CO_2CH_3$, $CO_2C_2H_5$, $SCCl_3$, $SO_2CH_3$, $SO_2C_2H_5$, $CH_2OCH_3$, $CH_2OOC_2H_5$, $CH_2CH_2OCH_3$, $COCH_2OCH_3$, $CH_2COOCH_3$, $SNHCH_3$, $SN(CH_3)_2$, $COCH_2CO_2H$, $COCH_2CO_2CH_3$, $COCH_2CH_2CO_2H$, $COCH_2CH_2CO_2CH_3$, $COCHCH_3CO_2H$, $COCHCH_3CO_2CH_3$, $COC_6H_4CO_2H$, $COC_6H_4CO_2CH_3$, $COCH=CHCO_2H$ or $COCH=CHCO_2CH_3$;

$R_2$ is selected from Cl, Br, F, $C_1$-$C_3$alkoxy, $C_1$-$C_3$haloalkoxy, $C_1$-$C_3$alkylamino, $C_1$-$C_3$haloalkylamino, $SCH_3$, $SC_2H_5$, $N(CH_3)_2$, $N(C_2H_5)_2$, $OCH_2OCH_3$, OPh, NHPh, $OCH_2Ph$, $NHCH_2Ph$, 4-chlorophenoxy, 4-chlorophenylamino, 2-chloro-4-(trifluoromethyl)phenoxy, 2-chloro-4-(trifluoromethyl)phenylamino, 3-chloro-5-(trifluoromethyl)pyridin-2-yloxy or 3-chloro-5-(trifluoromethyl)pyridin-2-ylamino;

$R_3$ is $NO_2$, $R_4$ and $R_8$ may be the same or different, respectively selected from H, Cl, Br, F, CN, $NO_2$, $C(=O)NH_2$, $C(=O)NHCH_3$, $C(=O)N(CH_3)_2$, $CH_3$, $C_2H_5$, $CF_3$, $OCH_3$, $OC_2H_5$, $OCF_3$, $SO_2CH_3$, $SO_2C_2H_5$, $COCH_3$, $COC_2H_5$, $CO_2CH_3$, $CO_2C_2H_5$, OPh, NHPh, $CO_2Ph$ or CONHPh;

$R_5$ and $R_7$ may be the same or different, respectively selected from H, Cl, Br, F, CN, $NO_2$, $C(=O)NH_2$, $CH_3$, $CF_3$, $OCH_3$, $OCF_3$, $NHCH_3$, $SCH_3$, $SO_2CH_3$, $SO_2C_2H_5$, $COCH_3$, $COC_2H_5$, $CO_2CH_3$, $CO_2C_2H_5$ or $CH_2OCH_3$;

$R_6$ is selected from H, Cl, Br, F, CN, $NO_2$, $CO_2H$, $C(=O)NH_2$, $C(=O)NHCH_3$, $C(=O)N(CH_3)_2$, $CH_3$, $CF_3$, $CF(CF_3)_2$, $OCF_3$, $OCH_2CF_3$, $OCF_2CHFCF_3$, $SO_2CH_3$, $SO_2C_2H_5$, $COCH_3$, $COC_2H_5$, $CO_2CH_3$, $CO_2C_2H_5$, OPh, NHPh, COPh, $COCH_2Ph$, $CO_2Ph$, CONHPh, pyridinoxy or 3-chloro-5-(trifluoromethyl)pyridin-2-yloxy;

but $R_4$, $R_5$, $R_6$, $R_7$ and $R_8$ can not be H simultaneously;

or the salts formed from the compounds of general formula I with hydrochloric acid, sulfuric acid, phosphoric acid, trifluoroacetic acid, methylsulfonic acid or p-toluenesulfonic acid.

6. A fungicidal composition comprising the compound according to claim 1 as an active ingredient and an acceptable carrier in agriculture, wherein the weight percentage of the active ingredient in the composition is 0.5-90%.

* * * * *